(12) United States Patent  (10) Patent No.: US 8,206,353 B2
Chong et al.  (45) Date of Patent: Jun. 26, 2012

(54) RESERVOIR BARRIER LAYER SYSTEMS AND METHODS

(75) Inventors: Colin A. Chong, Burbank, CA (US); Eric M. Lorenzen, Granada Hills, CA (US); Rafael Bikovsky, Oak Park, CA (US); Truong Gia Luan, Winnetka, CA (US); Arsen Ibranyan, Glendale, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 103 days.

(21) Appl. No.: 12/547,315

(22) Filed: Aug. 25, 2009

(65) Prior Publication Data

US 2010/0016791 A1 Jan. 21, 2010

Related U.S. Application Data

(63) Continuation-in-part of application No. 12/360,077, filed on Jan. 26, 2009.

(60) Provisional application No. 61/044,292, filed on Apr. 11, 2008.

(51) Int. Cl.
*A61M 1/00* (2006.01)
(52) U.S. Cl. ........................................ 604/152
(58) Field of Classification Search ............... 604/93.01
See application file for complete search history.

(56) References Cited

U.S. PATENT DOCUMENTS

| | | | |
|---|---|---|---|
| 1,935,494 A | 1/1900 | West | |
| 2,756,748 A | 1/1900 | Ferguson | |
| 1,182,042 A | 5/1916 | Rubin | |
| 3,075,528 A | 1/1963 | Isak et al. | |
| 3,886,938 A | 6/1975 | Szabo et al. | |
| 4,363,329 A | 12/1982 | Raitto | |
| 4,911,695 A | 3/1990 | Lindner | |
| 5,925,732 A | 7/1999 | Ecker et al. | |
| 5,957,889 A | 9/1999 | Poulsen et al. | |
| 6,088,608 A | 7/2000 | Schulman et al. | |
| 6,119,028 A | 9/2000 | Schulman et al. | |
| 6,416,323 B1 * | 7/2002 | Grenfell et al. | 433/90 |
| 6,585,700 B1 | 7/2003 | Trocki et al. | |
| 6,589,229 B1 | 7/2003 | Connelly et al. | |
| 6,740,072 B2 | 5/2004 | Starkweather et al. | |
| 6,827,702 B2 | 12/2004 | Lebel et al. | |
| 7,318,816 B2 | 1/2008 | Bobroff et al. | |

(Continued)

FOREIGN PATENT DOCUMENTS

DE 23 28 718 A1 1/1975

(Continued)

OTHER PUBLICATIONS

The PCT International Search Report for Application No. PCT/US2009/038177 dated Jan. 18, 2010.

(Continued)

*Primary Examiner* — Nicholas Lucchesi
*Assistant Examiner* — Melissa A Snyder
(74) *Attorney, Agent, or Firm* — Foley & Lardner LLP

(57) ABSTRACT

A system for delivering fluidic media may include a reservoir disposed within a housing, the reservoir having at least one wall bordering an interior volume for containing fluidic media, the wall being made of a material comprising a cyclic olefin copolymer, the wall for substantially preventing light from passing through the material of the wall. Fluidic media contained in the interior volume may be expelled through a fluid conduit.

26 Claims, 17 Drawing Sheets

U.S. PATENT DOCUMENTS

| | | |
|---|---|---|
| 7,323,142 B2 | 1/2008 | Pendo et al. |
| 7,455,663 B2 | 11/2008 | Blkovsky |
| 7,460,350 B2 | 12/2008 | Talbot et al. |
| 2001/0041869 A1 | 11/2001 | Causey et al. |
| 2001/0056264 A1 | 12/2001 | Sayama et al. |
| 2002/0016572 A1 | 2/2002 | Beebe |
| 2002/0022855 A1 | 2/2002 | Bobroff et al. |
| 2002/0193679 A1 | 12/2002 | Malave et al. |
| 2003/0097096 A1* | 5/2003 | Niedospial, Jr. ............. 604/218 |
| 2003/0125672 A1 | 7/2003 | Adair et al. |
| 2003/0170410 A1 | 9/2003 | Buch-Rasmussen et al. |
| 2003/0212364 A1 | 11/2003 | Mann et al. |
| 2003/0233075 A1 | 12/2003 | Huegli |
| 2004/0002682 A1 | 1/2004 | Kovelman et al. |
| 2004/0028856 A1 | 2/2004 | Smith et al. |
| 2004/0073095 A1 | 4/2004 | Causey et al. |
| 2005/0043689 A1 | 2/2005 | Chen |
| 2005/0065760 A1 | 3/2005 | Murtfeldt et al. |
| 2005/0157024 A1* | 7/2005 | Silverbrook et al. ........... 347/40 |
| 2005/0197626 A1 | 9/2005 | Moberg et al. |
| 2006/0229583 A1 | 10/2006 | Nagao |
| 2006/0253085 A1 | 11/2006 | Geismar et al. |
| 2006/0264894 A1 | 11/2006 | Moberg et al. |
| 2006/0293687 A1 | 12/2006 | Bogert |
| 2007/0078319 A1 | 4/2007 | Shah et al. |
| 2007/0219508 A1 | 9/2007 | Bisegna |
| 2008/0026592 A1 | 1/2008 | Shah et al. |
| 2008/0039822 A1 | 2/2008 | Zhang et al. |
| 2008/0050281 A1 | 2/2008 | Pendo et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051738 A1 | 2/2008 | Griffin |
| 2008/0051765 A1 | 2/2008 | Mounce |
| 2008/0055111 A1 | 3/2008 | Morgan et al. |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0221509 A1 | 9/2008 | Gottlieb et al. |
| 2008/0264261 A1 | 10/2008 | Kavazov et al. |
| 2008/0265859 A1 | 10/2008 | Talbot et al. |
| 2008/0269680 A1 | 10/2008 | Lbranyan et al. |
| 2008/0269681 A1 | 10/2008 | Kavazov et al. |
| 2008/0269682 A1 | 10/2008 | Kavazov et al. |
| 2008/0269683 A1 | 10/2008 | Bikovsky |
| 2008/0269687 A1 | 10/2008 | Chong et al. |
| 2008/0269713 A1 | 10/2008 | Kavazov |
| 2008/0289300 A1 | 11/2008 | Gottlieb et al. |
| 2009/0005666 A1 | 1/2009 | Shin et al. |
| 2009/0030297 A1 | 1/2009 | Miller et al. |
| 2009/0036870 A1 | 2/2009 | Mounce et al. |
| 2009/0081753 A1 | 3/2009 | Shah et al. |
| 2009/0082728 A1 | 3/2009 | Bikovsky |
| 2009/0098643 A1 | 4/2009 | Mastrototaro et al. |
| 2009/0163878 A1 | 6/2009 | Moberg et al. |
| 2009/0171291 A1 | 7/2009 | Bent, IV et al. |
| 2009/0171324 A1 | 7/2009 | Chong et al. |
| 2009/0172640 A1 | 7/2009 | Geismar et al. |

FOREIGN PATENT DOCUMENTS

| | | |
|---|---|---|
| DE | 24 58 004 A1 | 6/1976 |
| DE | 1020060 45 959 B3 | 1/2008 |
| EP | 0 110 687 B1 | 10/1986 |
| EP | 0 264 273 B1 | 4/1988 |
| EP | 0 925 798 B1 | 6/1999 |
| EP | 1 293 223 A1 | 3/2003 |
| EP | 1 488 818 A | 12/2004 |
| FR | 1041436 A | 10/1953 |
| FR | 1097841 A | 7/1955 |
| FR | 1104570 A | 11/1955 |
| JP | 07-178854 A | 7/1995 |
| JP | 2003-180832 A | 7/2003 |
| WO | WO-85/02256 A | 5/1985 |
| WO | WO-88/05315 A | 7/1988 |
| WO | WO-93/04951 A | 3/1993 |
| WO | WO-00/47254 A1 | 8/2000 |
| WO | WO-01/70307 A1 | 9/2001 |
| WO | WO-2004/030716 A2 | 4/2004 |
| WO | WO-2004/030717 A2 | 4/2004 |
| WO | WO-2006/024650 A2 | 3/2006 |
| WO | WO-2008/024814 A2 | 2/2008 |
| WO | WO-2009/068251 A1 | 6/2009 |
| WO | WO-2009/126435 A2 | 10/2009 |

OTHER PUBLICATIONS

The PCT International Search Report for Application No. PCT/US2009/039714 dated Oct. 2, 2009.

US Office Action dated Apr. 7, 2010 from related U.S. Appl. No. 12/417,976.

US Office Action dated Sep. 27, 2010 from related U.S. Appl. No. 12/417,976.

Partial Search Report dated Jan. 12, 2011 from related PCT application No. PCT/US2010/044021.

Search Report dated Feb. 1, 2011 from related PCT application No. PCT/US2010/046530.

US Office Action dated Jun. 27, 2011 from related U.S. Appl. No. 12/360,077.

Search Report dated Mar. 15, 2011 from related PCT Application No. PCT/US2010/044021.

* cited by examiner

RESERVOIR BARRIER LAYER SYSTEMS AND METHODS

CROSS-REFERENCE TO RELATED PATENT APPLICATIONS

This application is a Continuation-In-Part of U.S. application Ser. No. 12/360,077, filed Jan. 26, 2009, incorporated herein by reference in its entirety, which claims priority from Provisional Application U.S. Application 61/044,292, filed Apr. 11, 2008, incorporated herein by reference in its entirety.

BACKGROUND

1. Field of the Invention

Embodiments of the present invention relate generally to systems and methods with reservoirs and, in specific embodiments, to systems and methods with reservoirs with multiple layers, including, but not limited to, reservoirs in pen-like injection devices.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. In recent times, modern systems have been designed to include programmable pumps for delivering controlled amounts of medication to a patient.

Pump-type delivery devices have been configured in external devices, which connect to a patient, and have been configured in implantable devices, which are implanted inside of the body of a patient. External pump-type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin. External pump-type delivery devices may be connected in fluid flow communication to a patient or user-patient, for example, through a suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a user-patient, for example, through a suitable hollow tubing. The hollow tubing may be connected to a hollow needle that is designed to pierce the user-patient's skin and deliver an infusion medium to the user-patient. Alternatively, the hollow tubing may be connected directly to the user-patient as or through a cannula or set of micro-needles.

In contexts in which the hollow tubing is connected to the user-patient through a hollow needle that pierces the user-patient's skin, a manual insertion of the needle into the user-patient can be somewhat traumatic to the user-patient. Accordingly, insertion mechanisms have been made to assist the insertion of a needle into the user-patient, whereby a needle is forced by a spring to quickly move from a retracted position into an extended position. As the needle is moved into the extended position, the needle is quickly forced through the user-patient's skin in a single, relatively abrupt motion that can be less traumatic to certain user-patients as compared to a slower, manual insertion of a needle. While a quick thrust of the needle into the user-patient's skin may be less traumatic to some patient's than a manual insertion, it is believed that, in some contexts, some patients may feel less trauma if the needle is moved a very slow, steady pace. Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump type delivery devices can be significantly convenient to a user-patient, in that accurate doses of insulin may be calculated and delivered automatically to a user-patient at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and as doctors and user-patients become more familiar with such devices, the popularity of external medical infusion pump treatment increases and is expected to increase substantially over the next decade.

SUMMARY OF THE DISCLOSURE

A system for delivering fluidic media may include a housing, a reservoir, and a fluid conduit. The reservoir may be disposed within the housing. The reservoir may have at least one wall bordering an interior volume for containing fluidic media. The wall may be made of a material comprising a cyclic olefin copolymer. The material of the wall may substantially prevent light from passing through the material of the wall. The fluid conduit may be in communication with the interior volume of the reservoir for allowing fluidic media contained in the interior volume to be expelled from the reservoir.

In various embodiments, the fluid conduit may comprise a needle. In various embodiments, the reservoir may be removable from the housing. In various embodiments, the wall may comprise at least one layer made of a material that is not a cyclic olefin copolymer. In various embodiments, the wall may be opaque to substantially prevent light from passing through the material of the wall. In various embodiments, the wall may be adapted to be at least one of frosted, textured, and etched to substantially prevent light from passing through the material of the wall. In various embodiments, the wall may have a light transmission at 400 nm of less than 25%.

In various embodiments, the wall of the reservoir may have at least one window for allowing light to pass into the interior volume of the reservoir. In some embodiments, the reservoir may have a circular cross-section circumference. The at least one window may have a width dimension corresponding to less than a quarter of the circular cross-section circumference of the reservoir. In some embodiments, the at least one window may have a width dimension corresponding to an angle of less than 90° relative to a central axis of the reservoir.

In some embodiments, the at least one window may be for providing a viewing angle into the interior volume of the reservoir of less than 90° relative to a central axis of the reservoir. In some embodiments, the at least one window may comprise a plurality of windows. Each of the plurality of windows may be offset less than 90° relative to a central axis of the reservoir from any other window of the plurality of windows.

In some embodiments, the housing may be sufficiently transparent for allowing light to pass through the housing and the window in the reservoir into the interior volume of the reservoir. In some embodiments, the housing may have at least one window for allowing light to pass through the at least one window of the housing and the at least one window in the reservoir into the interior volume of the reservoir. In further embodiments, the at least one window of the housing may be adjacent and facing the at least one window of the reservoir.

In some embodiments, the window may have a width dimension extending partially around a central axis of the reservoir. The width dimension may be between a first width edge and a second width edge. The first width edge may be linearly spaced from the central axis of the reservoir in a first linear dimension, and the second width edge may be linearly spaced from the central axis of the reservoir in a second linear dimension. The first linear dimension and the second linear dimension may be at an angle of less than 90° relative to each other.

In various embodiments, the system may further include a drive mechanism for forcing fluidic media from the interior volume of the reservoir out the fluid conduit in a case where the interior volume of the reservoir contains fluidic media and the drive mechanism is activated.

A method of manufacturing a system for delivering fluidic media may include (but is not limited to) any one of or combination of: (i) providing a housing; (ii) disposing a reservoir within the housing, the reservoir having at least one wall bordering an interior volume for containing fluidic media, the wall being made of a material comprising a cyclic olefin copolymer, the wall for substantially preventing light from passing through the material of the wall; and (iii) providing a fluid conduit in communication with the interior volume of the reservoir for allowing fluidic media contained in the interior volume of the reservoir to be expelled from the reservoir. In various embodiments, the wall of the reservoir may have at least one window for allowing light to pass into the interior volume of the reservoir.

DETAILED DESCRIPTION

Figure 1:
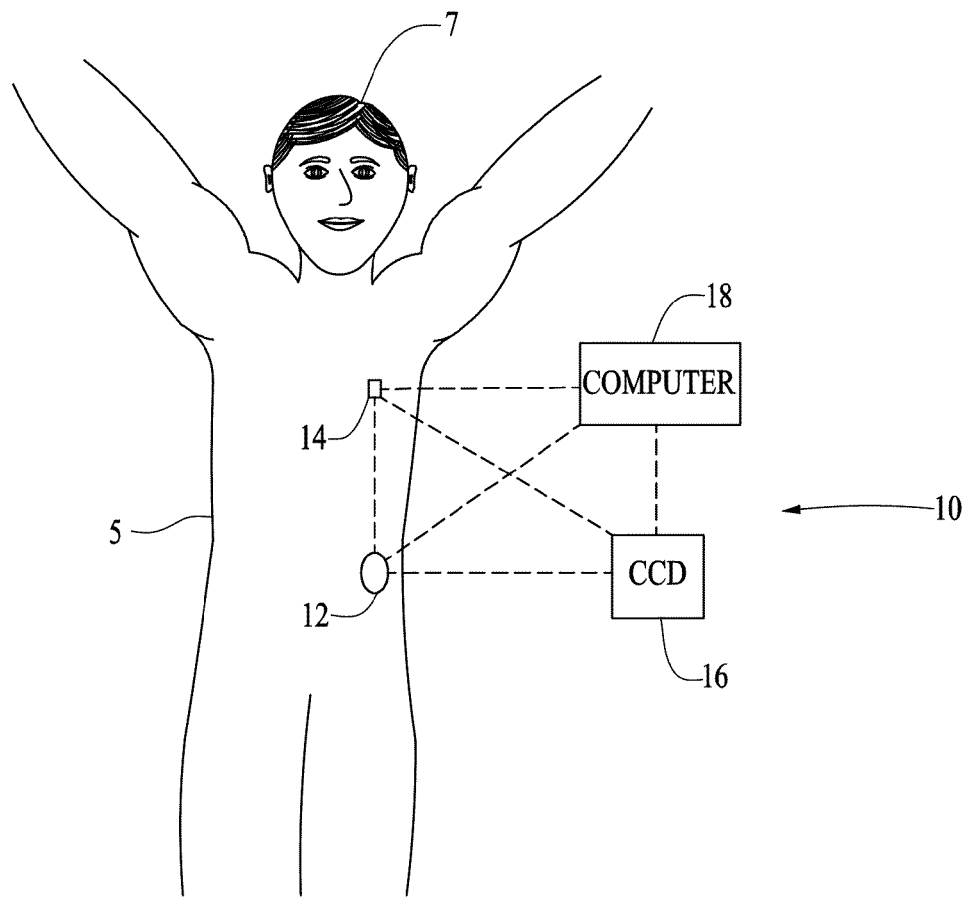
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. patent applications that were assigned to the assignee of the present invention, however, with a reservoir configuration such as described herein (e.g., FIGS. 7-8C), where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588, 847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604, 172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645, 993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir"'; (xx) U.S. patent application Ser. No. 11/606, 837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924, 402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121, 647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044, 292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179, 536, filed Jul. 24, 2008, "Real Time Self-Adjusting Calibration Algorithm"; (xlvii) U.S. patent application Ser. No.

12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S. patent application Ser. No. 12/360,813, filed Jan. 27, 2009, "Multi-Position Infusion Set Device And Process." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
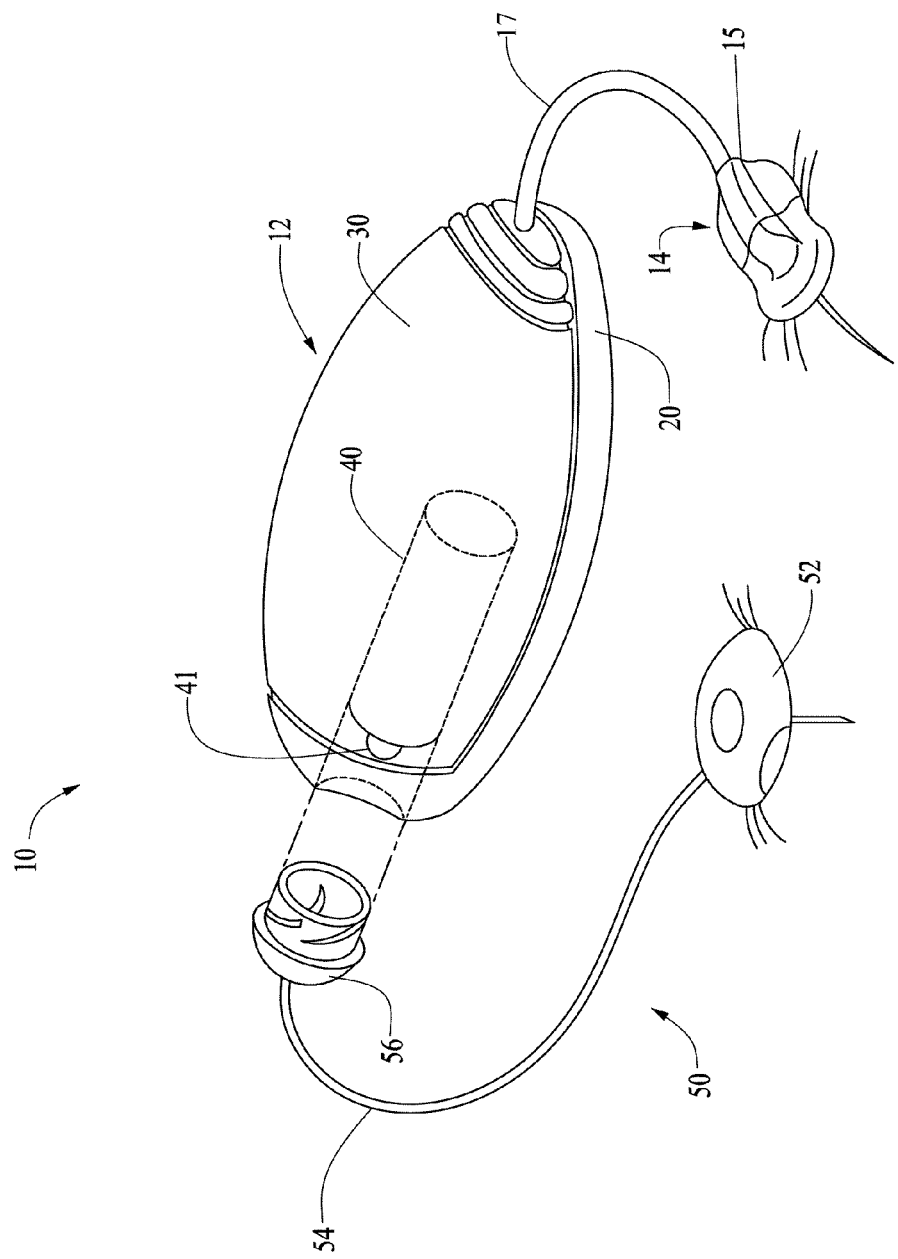
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 includes a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. In addition, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, to provide a seal against water entering between the durable housing 30 and the disposable housing 20.

The durable housing 30 of the delivery device 12 may support a drive device (not shown in FIG. 2) including a motor and a drive device linkage portion for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
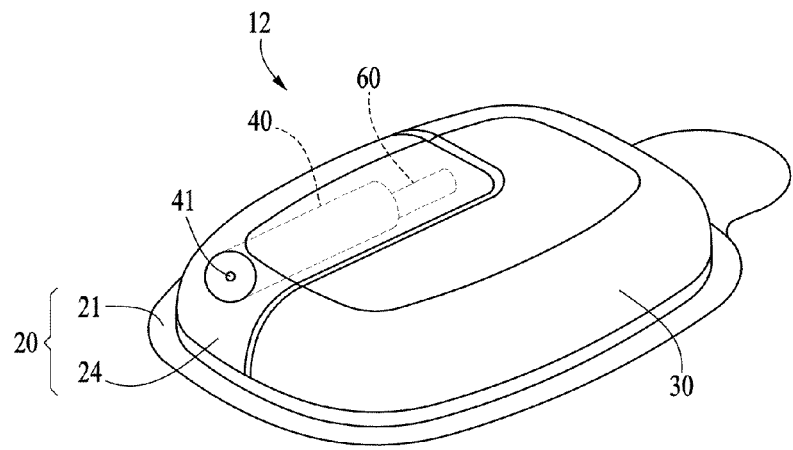
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir retaining portion 24 of the disposable housing 20 may be configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
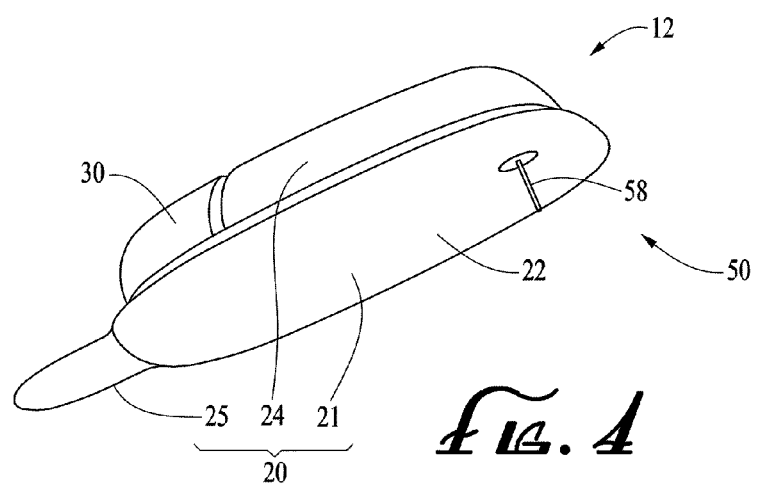
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
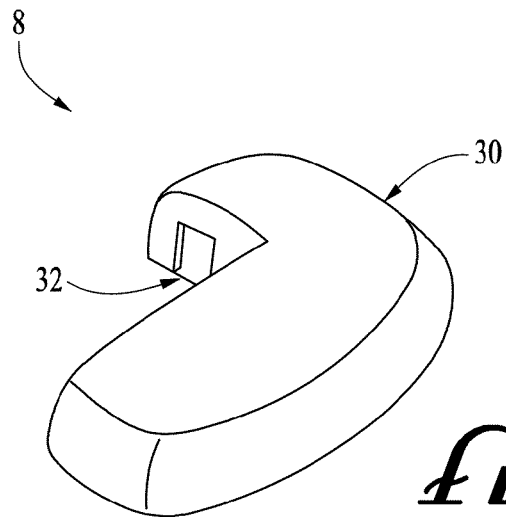
FIG. 5A illustrates a durable portion of a delivery device in accordance with an embodiment of the present invention.
Figure 5B:
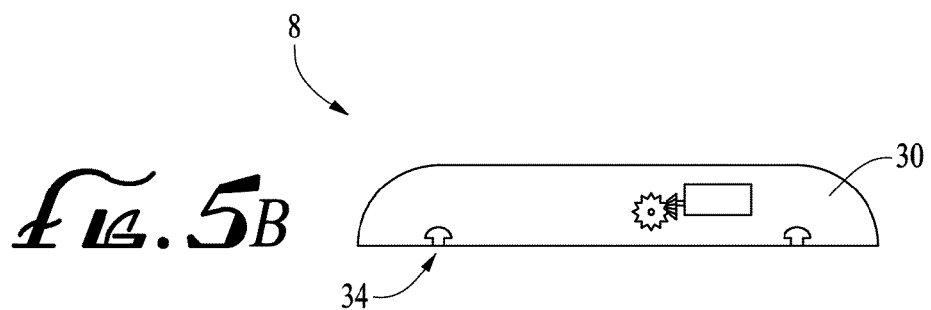
FIG. 5B illustrates a section view of a durable portion of a delivery device in accordance with an embodiment of the present invention.
Figure 5C:
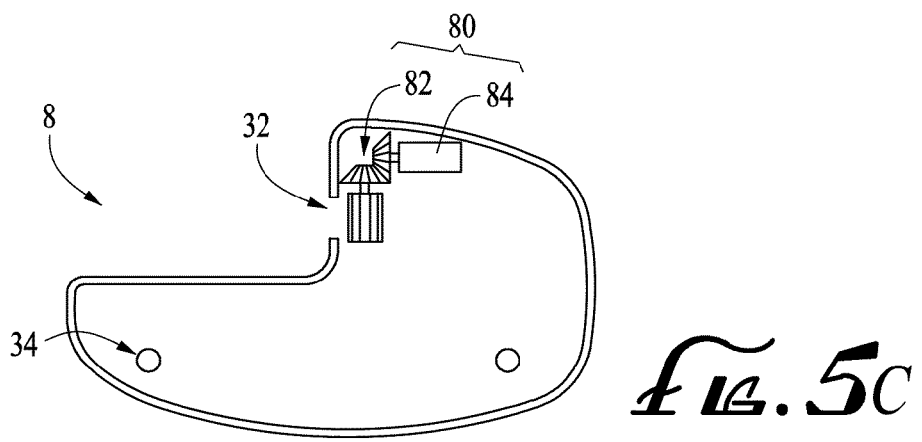
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 is configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
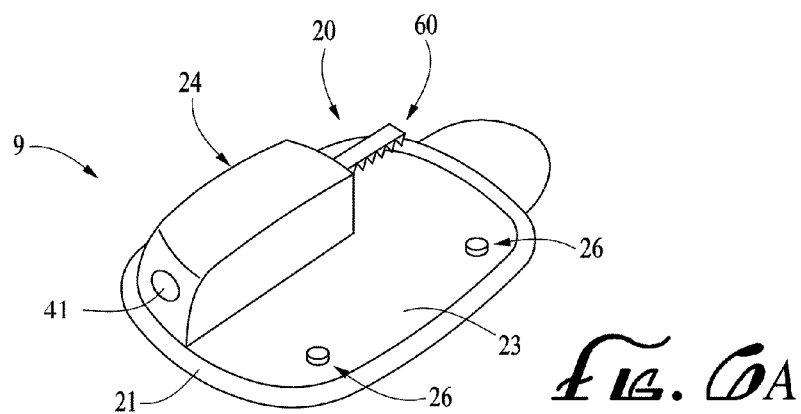
FIG. 6A illustrates a disposable portion of a delivery device in accordance with an embodiment of the present invention.
Figure 6B:
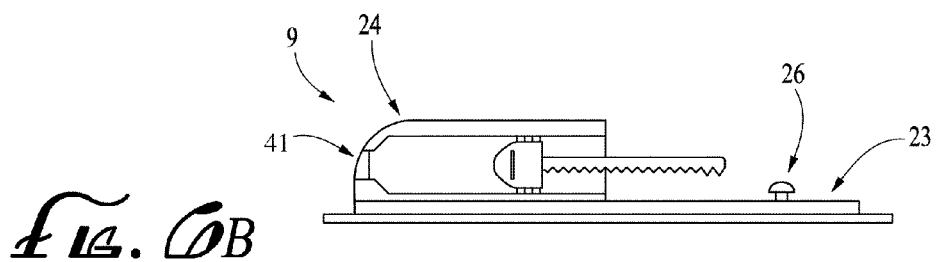
FIG. 6B illustrates a section view of a disposable portion of a delivery device in accordance with an embodiment of the present invention.
Figure 6C:
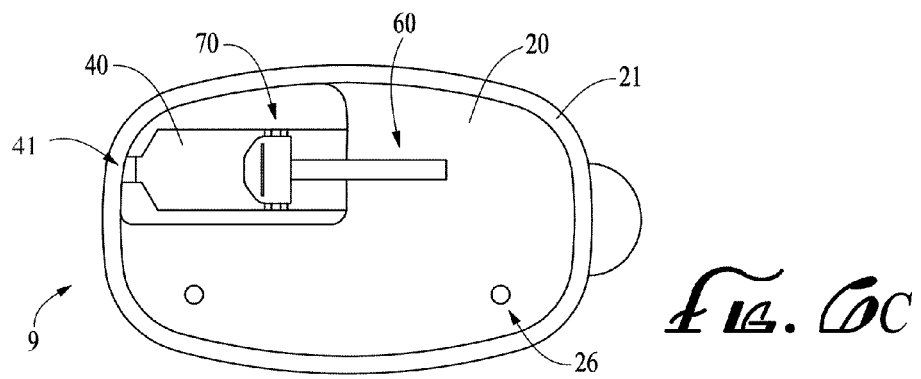
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir-retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. In addition, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir-retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry is further configured to store data to the reservoir circuitry after at least some of the contents of the reservoir system 40 have been transferred out of the reservoir system 40, so as to update information in the reservoir circuitry related to an amount of contents still remaining in the reservoir system 40. In some embodiments, the reservoir status circuitry is configured to store data to the reservoir circuitry, to update information in the reservoir circuitry related to an amount of contents remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

Figure 7:
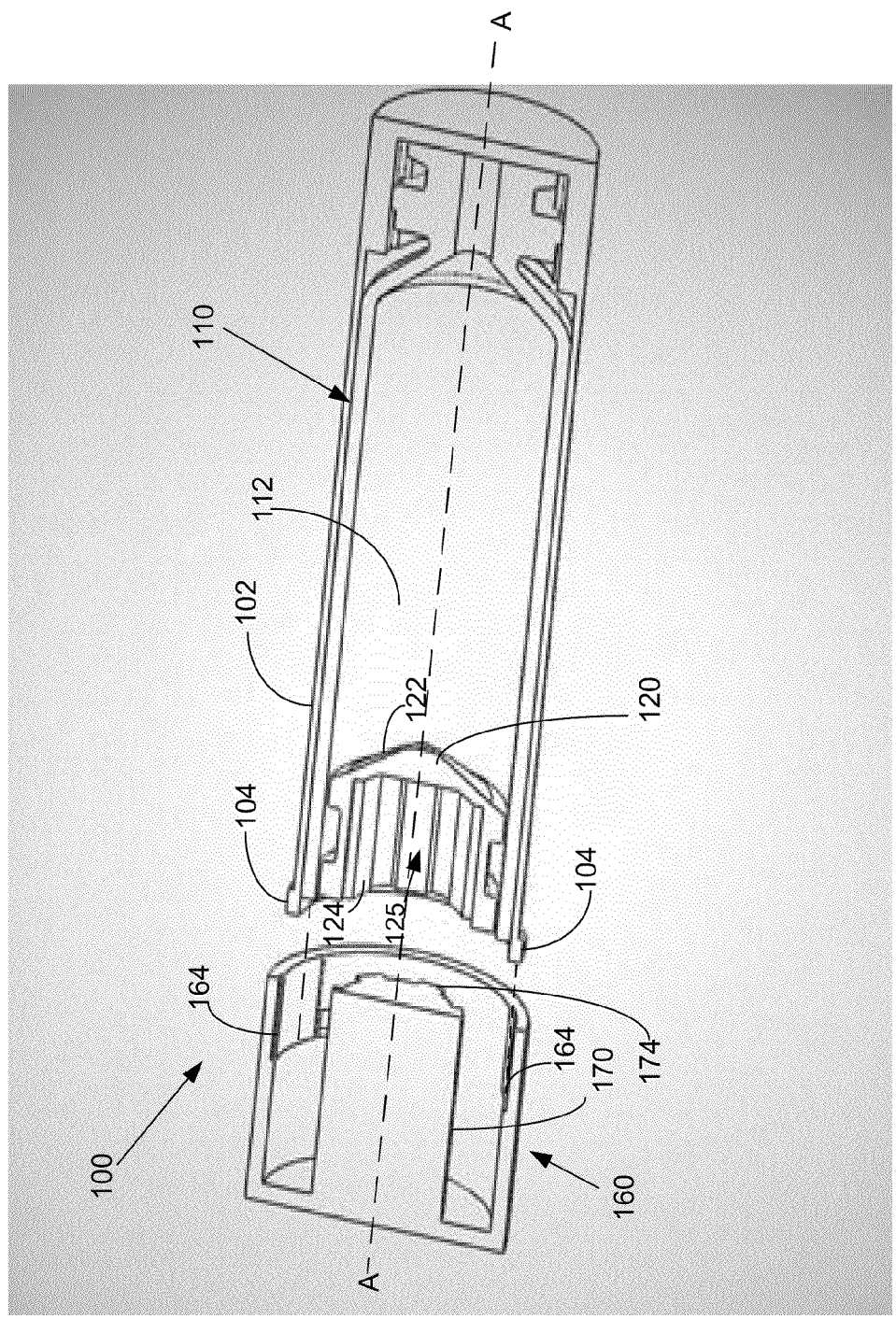
FIG. 7 illustrates a system for containing fluidic media in accordance with an embodiment of the present invention.

FIG. 7 illustrates a reservoir system 100 that may be employed as an embodiment of the reservoir system 40 discussed above, for containing fluidic media in accordance with an embodiment of the present invention. The reservoir system 100 may include, but is not limited to, a casing 102, a reservoir body 110, a plunger head 120, a base 160, and a plunger support 170.

The reservoir body 110 may have an interior volume 112 for containing fluidic media. The reservoir body 110 may be pre-filled with fluidic media prior to the reservoir body 110 being installed in or otherwise used with a delivery device (not shown). The reservoir body 110 may have a port for expelling fluidic media contained in the interior volume 112 of the reservoir body 110. In various embodiments, the reservoir body 110 may be made of various suitable materials, including, but not limited to, glass, plastic, TOPAS® polymers, or the like.

The reservoir body 110 may be adapted to store fluidic media for a specific duration of time, for example days, weeks, months, or longer depending on needs of user-patients. The reservoir body 110 may be of any suitable shape and/or size and may be adapted to hold any volume depending on needs of user-patients. In various embodiments, the reservoir body 110 may be adapted to store fluidic media external to the human body.

The reservoir body 110 may be located within the casing 102. The casing 102 may enclose the reservoir body 110 partially or in its entirety. In other embodiments, the casing 102 may be omitted. In some embodiments, the casing 102 may be removed from the reservoir body 110 before the reservoir body 110 is used with the delivery device (not shown). In other embodiments, the casing 102 may remain on the reservoir body 110 while the reservoir body 110 is used with the delivery device (not shown).

In some embodiments, the casing 102 may be for protecting the reservoir body 110. In further embodiments, the casing 102 may be a barrier to inhibit infusion or diffusion of substances into or out of the reservoir body 110. For example, the casing 102 may be configured to prevent preservatives or the like from diffusing or "leeching" out from the interior volume 112 of the reservoir body 110. In yet further embodiments, the casing 102 may be for protecting a septum of the reservoir, for example keeping the septum sterile. In further embodiments, the casing 102 may protect the plunger head 120, for example from accidental movement of the plunger head 120.

The plunger head 120 may be located within the reservoir body 110 and may be moveable in an axial direction of the reservoir body 110 to expand or contract the interior volume 112 of the reservoir body 110. The plunger head 120 may be advanced within the reservoir body 110 to expel fluidic media contained in the interior volume 112 of reservoir body 110 out the port of the reservoir body 110. In various embodiments where the reservoir body 110 is pre-filled with fluidic media, the plunger head 120 may be made of Bromobutyl rubber, silicone rubber, or any other suitable material and/or any derivative thereof.

The plunger head 120 may have a front surface 122. The front surface 122 of the plunger head 120 may be in contact with fluidic media contained in the interior volume 112 of the reservoir body 110. The plunger head 120 may have a hollow interior 125 on an opposite side from the front surface 123 of the plunger head 120.

The plunger head 120 may be configured to be removably attachable or otherwise connectable to the plunger support 170. For example, the plunger head 120 may include mating teeth 124 located within the hollow interior 125 of the plunger head 120. The plunger support 170 may include mating teeth 174 to complement or otherwise engage the mating teeth 124 of the plunger head 120 to allow the plunger support 170 to be inserted within the hollow interior 125 of the plunger head 120. In some embodiments, when in engaged, the mating teeth 174 of the plunger support 170 and the mating teeth 124 of the plunger head 120 may be for restricting a movement, such as, but not limited to, a rotational or a longitudinal movement, of the plunger head 120 relative to the reservoir body 110. In other embodiments, the reservoir system 100 may offer any suitable mating shapes and/or configurations that inhibit relative rotation or other movement between the plunger head 120 and the reservoir body 110.

The plunger support 170 may be connected to the base 160. In some embodiments, the plunger support 170 and the base 160 may be integral to each other. In some embodiments, the base 160 and/or the plunger support 170 may be configured to receive at least a portion of the reservoir body 110. In further embodiments, the base 160 and/or the plunger support 170 may be configured to receive at least a portion of the casing 102 containing the reservoir body 110.

In some embodiments, the casing 102 may include a connection structure that removably attaches the casing 102 to the base 160. In addition, the connection structure may allow for removal of the casing 102 from the base 160. For example, in some embodiments, the casing 102 may include one or more locking tabs 104 and the base 160 may include one or more recesses 164, apertures, or the like, for receiving the locking tabs 104 of the casing 102. In such embodiments, the casing 102 containing the reservoir body 110 may be placed at least partially within the base 160 to fit the locking tabs 104 of the casing 102 within the recesses 164 of the base 160. Once the locking tabs 104 of the casing 102 reach an end of the recesses 164 of the base 160, the casing 102, for example, may be then rotated to lock the casing 102 and reservoir body 110 to the base 160. Accordingly, the casing 102 and the reservoir body 110 may remain locked to the base 160 until a user-patient removes the casing 102 and reservoir body 110, for example by rotating the casing 102 in an opposite direction and then removing the casing 102 and the reservoir body 110 from the base 160. In other embodiments, the locking tabs 104 and recesses 164 can be reversed in the casing 102 and the base 160. In yet other embodiments, any combination of tabs 104 and recesses 164 can be utilized with the casing 102 and the base 160.

The plunger head 120 and the reservoir body 110 may have a certain frictional retaining force (or stiction) between each other. Advancement or movement of the plunger head 120 may be facilitated by at least partially reducing the frictional retaining force. As such, the plunger head 120 may be primed for use, for example, in a case where the reservoir body 110 is placed within the delivery device (not shown) and fluidic media is to be expelled out the port of the reservoir body 110. Thus, in some embodiments, the plunger head 120 and/or the reservoir body 110 may be configured to be moved relative to one another when and/or in response to detaching the reservoir body 110 and/or the casing 102 containing the reservoir body 110 from the base 160. Accordingly, the frictional retaining force (or stiction) between the plunger head 120 and the reservoir body 110 may be reduced at least partially to facilitate advancement of the plunger head 120.

In some embodiments, the plunger head 120 and/or the reservoir body 110 may be configured to move rotatably relative to one another to reduce the frictional retaining force between the plunger head 120 and the reservoir body 110, for example, in a clockwise or a counter-clockwise direction.

For example, as previously discussed the mating teeth 124 within the hollow interior 125 of the plunger head 120 may be engaged with the complementing mating teeth 174 of the plunger support 170. Thus, the mating teeth 124 of the plunger head 120 and the complementing mating teeth 174 of the plunger support 170 may engage each other and prevent the plunger head 120 from rotating about the reservoir body 110 in a case where the casing 102 containing the reservoir body 110 is connected to the base 160 and the casing 102 is rotated, for example, when the casing 102 is removed from the base 160. Thus, when the casing 102 containing the reservoir body 110 is rotated while the plunger head 120 is prevented from rotating by the plunger support 170, the frictional retaining force between the reservoir body 110 and the plunger head 120 may be reduced as the reservoir body 110 is allowed to rotate relative to the plunger head 120. The reservoir body 110 having a reduced frictional retaining force with the plunger head 120 is primed and may then be placed in the delivery device (not shown).

In some embodiments, the user-patient may hold the base 160 and the casing 102 and rotate one of the base 160 and the casing 102 relative to the other. In other embodiments, the user-patient may hold the base 160 and the casing 102 and pull one of the base 160 and casing 102 apart from the other. In yet further embodiments, the user-patient may hold the base 160 and the casing 102 and do a relative twist of one of the base 160 and the casing 102 relative to the other, for example rotating and pulling apart one of the base 160 and the casing 102 relative to the other.

In some embodiments, the base 160 may be attached or otherwise be part of a packaging (not shown). The base 160 and/or the packaging may be configured to move the plunger head 120 relative to the reservoir body 110 when the casing 102 containing the reservoir body 110 is removed from the base 160 connected to the packaging. For example, in some embodiments, the packaging may be configured to hold the base 160. The casing 102 can then be removed from the base 160; leaving the base 160 attached to the packaging. Because the plunger head 120 is engaged with the plunger support 170, using any suitable manner, such as, but not limited to, the embodiments discussed, including complementing mating teeth 124 and 174, movement of the casing 102 containing the reservoir body 110, for example, to remove the casing 102 from the packaging may cause the reservoir body 110 to rotate relative to the plunger head 120. Accordingly, the frictional retaining force (or stiction) between the plunger head 120 and the reservoir body 110 may be reduced.

In some embodiments, the plunger head 120 and/or the reservoir body 110 may be configured to move longitudinally relative to one another to reduce the frictional retaining force between the plunger head 120 and the reservoir body 110. In such embodiments, the plunger support 170 may prevent the plunger head 120 from moving longitudinally along a lengthwise axis A of the reservoir body 110 relative to the reservoir body 110, for example, when the casing 102 is removed from the base 160. For example, the plunger support 170 may prevent the plunger head 120 from moving along the axis A relative to the reservoir body 110 in a case where the casing 102 containing the reservoir body 110 is operatively connected to the base 160 and the casing 102 is moved away from the base 160 along the axis A.

For example, the plunger support 170 and the plunger head 120 may have opposing mating teeth that interlock when engaged to hold the plunger head 120 to the plunger support 170 when the casing 102 containing the reservoir body 110 is moved away longitudinally from the base 160. As a result, the frictional retaining force between the reservoir body 110 and the plunger head 120 may be reduced as the reservoir body 110 is allowed to move longitudinally along the axis A relative to the plunger head 120. The reservoir body 110 having a reduced frictional retaining force with the plunger head 120 may then be placed in the delivery device (not shown).

In some embodiments, the base 160 may be attached or otherwise be part of a packaging, which may configured similar to the embodiments previously discussed. The base 160 and/or the packaging may be configured to move the plunger head 120 relative to the reservoir body 110 when the casing 102 containing the reservoir body 110 is removed from the base 160 connected to the packaging. For example, in some embodiments, the packaging may be configured to hold the base 160. The casing 102 can then be removed from the base 160; leaving the base 160 attached to the packaging. Because the plunger head 120 is engaged with the plunger support 170, in any suitable manner, such as, but not limited to, the embodiments discussed, including opposing teeth, movement of the casing 102 containing the reservoir body 110, for example to remove the casing 102 from the packaging may cause the reservoir body 110 to move longitudinally relative to the plunger head 120. Accordingly, the frictional retaining force (or stiction) between the plunger head 120 and the reservoir body 110 may be reduced.

In yet other embodiments, the plunger head 120 and/or the reservoir body 110 may be configured to move laterally and longitudinally along the axis A relative to one another to reduce the frictional retaining force between the plunger head 120 and the reservoir body 110. Such embodiments may be configured using, but is not limited to, any one or combination of frictional retaining force reduction structures previously discussed.

Figure 8A:
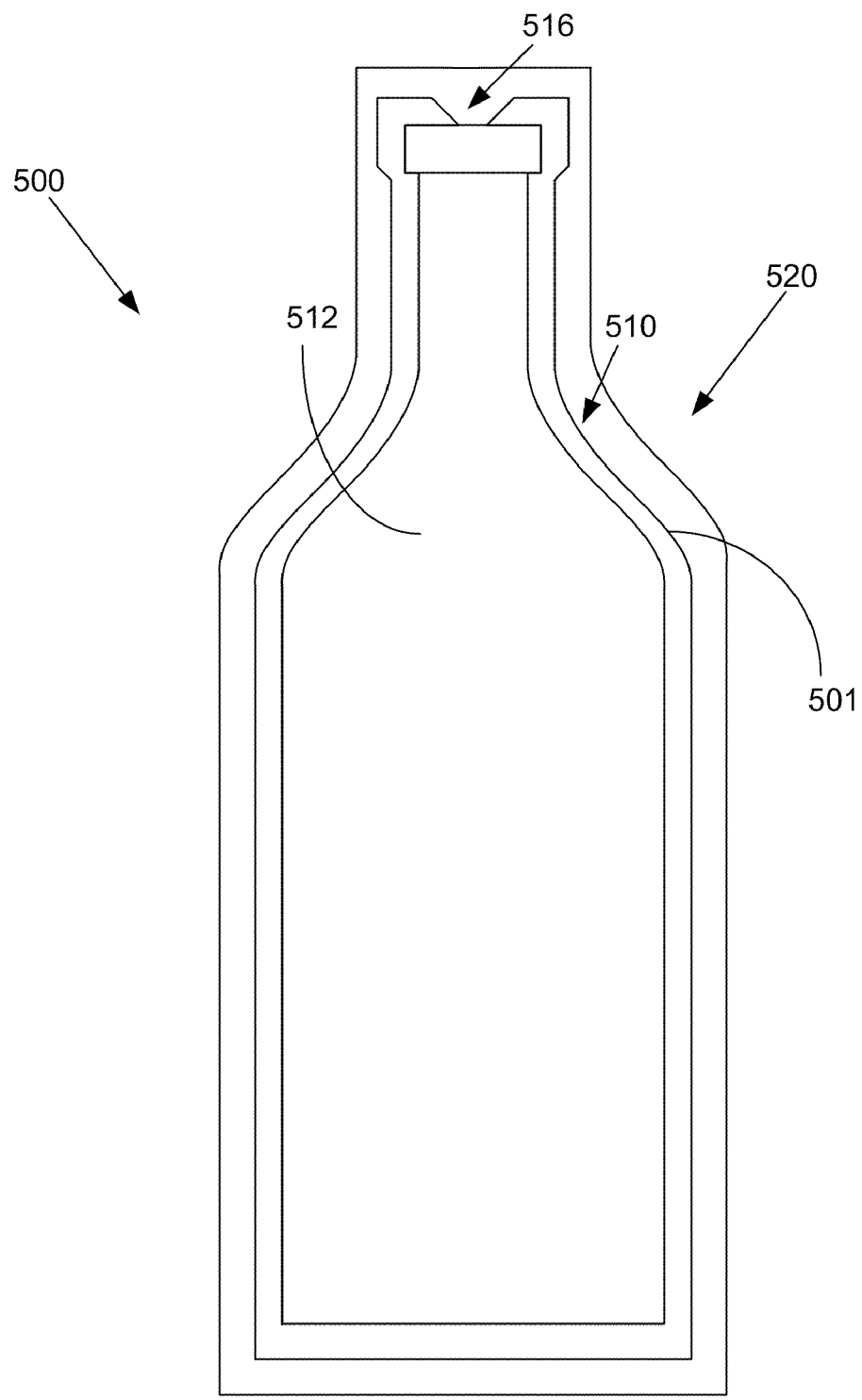
FIG. 8A illustrates a system for containing fluidic media in accordance with an embodiment of the present invention.

FIG. 8A illustrates a reservoir system 500 that may be employed as an embodiment of the reservoir system 40 discussed above, for containing fluidic media in accordance with an embodiment of the present invention. The reservoir system 500 may include, but is not limited to, a reservoir body 510 and an outer body 520. The reservoir body 510 may have a head portion 516.

The reservoir body 510 may comprise a container structure having a container wall 501 made of a first material. The container wall 501 may be shaped or otherwise configured to form the reservoir body 510. The reservoir body 510 may have an interior volume 512 for containing fluidic media, such as, but not limited to, insulin, or the like. The reservoir body 510 may have a port for expelling fluidic media contained in the interior volume 512 of the reservoir body 510, for example, through the head portion 516 of the reservoir body 510.

The reservoir body 510 may be pre-filled with fluidic media prior to the reservoir body 510 being used by a user-patient. The reservoir body 510 may be adapted to store fluidic media for a specific duration of time, for example days, weeks, months, or longer depending on needs of user-patients. The reservoir body 510 may be of any suitable shape and/or size and may be adapted to hold any volume depending on needs of user-patients. In various embodiments, the reservoir body 510 may be adapted to store fluidic media external to the human body.

The first material may be compatible with fluidic media contained in the reservoir body 510. In various embodiments, the reservoir body 510 may be made of various suitable materials, including, but not limited to, polyethylene, polystyrene, Teflon, glass, plastic, TOPAS® polymers, or the like. For example, with such materials, the reservoir body 510 may contain an insulin formula or other infusion medium compatible with such material. Other embodiments may be configured to contain other fluidic media, in which case, the material for the reservoir body 510 may be selected to be compatible with the fluidic media.

In various embodiments where the reservoir body 510 is pre-filled with fluidic media, the reservoir body 510 may include a plunger head (not shown) that may be attachable to a delivery device (not shown). In further embodiments, the plunger head may be placed in the reservoir body 510 before or after the reservoir body 510 is filled with fluidic media. The plunger head may be made of Bromobutyl rubber, silicone rubber, or any other suitable material and/or any derivative thereof.

In some embodiments, the plunger head may be configured, treated, or otherwise adapted to frictionally seal or engage an inner wall of the reservoir body 510 as the plunger head moves along the reservoir body 510. In further embodiments, the inner wall of the reservoir body 510 may be made of or treated with a cyclic olefin copolymer (or polymer), such as (but not limited to) TOPAS®, or the like. In such embodiments, the plunger head may be configured, treated, or otherwise adapted to interact with the inner wall of the reservoir body 510, for example, to frictionally seal or engage the inner wall of the reservoir body 510 as the plunger head moves along the reservoir body 510.

The outer body 520 may be or may include a barrier layer made of a second material different from the first material. The barrier layer may be shaped or otherwise configured to form the outer body 520. Thus in various embodiments, the outer body 520 may be a layer or wall section to form the reservoir body 510 along with the container wall 501, and in other embodiments, the outer body 520 may be a body separate from the reservoir body 510. The outer body 520 may be for receiving at least a portion of the reservoir body 510. In some embodiments, the outer body 520 may be formed on and/or supported by the reservoir body 510, as in the form of a layer, coating, film, or other structure on the reservoir body 510. Thus, in various embodiments, the reservoir system 500 may be a multi-layered structure (e.g., reservoir body 510 and outer body 520).

The outer body 520 may be adjacent the container wall 501. Thus in some embodiments, the outer body 520 may be adjacent the reservoir body 510. In some embodiments, the outer body 520 may be in firm contact with the container wall 501.

The outer body 520 may substantially cover the container wall 501. In some embodiments, the outer body 520 may be disposed outside the container wall 501. In various embodiments, the head portion 516 of the reservoir body 510 may be made of the first material of the container wall 501 and/or the second material of the outer body 520.

The outer body 520 may be for inhibiting diffusion of substances into and/or out of the interior volume 512 of the reservoir body 510. Thus, the properties, composition, and/or stability of fluidic media contained within the interior volume 512 of the reservoir body 510 may be more accurately maintained, controlled, and/or monitored. In some embodiments, the outer body 520 may be for inhibiting an outward diffusion of preservatives within fluidic media contained in the interior volume 512 of the reservoir body 510. In further embodiments, the outer body 520 may be for regulating an interaction between fluidic media contained in the interior volume 512 of the reservoir body 510 and the outer body 520, for example through the use of hydrophobic or hydrophilic materials.

In some embodiments, the outer body 520 may be configured to cover entirely the reservoir body 510 including the head portion 516 of the reservoir body 510. In some embodiments, the outer body 520 may be any suitable gas for inhibiting diffusion of substances into and/or out of the interior volume 512 of the reservoir body 110.

In some embodiments, the material comprising the outer body 520 may be selected from a group of halogenated polymers such as, but not limited to, polytetrafluorethylene (PTFE Teflon), polyvinylidene chloride (Saran), polyvinylidene fluoride (Kynar), or derivatives of any of these materials. In some embodiments, the material comprising the outer body 520 may comprise polymeric materials such as, but not limited to, polyamides, ethylene-vinyl alcohol (EVOH), polyetheretherketone (PEEK), nylon, polyester, or derivatives of any of these materials. In some embodiments, the material comprising the outer body 520 may comprise inorganic materials such as, but not limited to, capillary glass or diamond coated materials, or the like. In some embodiments, the material comprising the outer body 520 may comprise a cyclic olefin copolymer (or polymer), such as (but not limited to) a TOPAS® polymer; a metal, such as (but not limited to) a metallic foil (e.g., aluminum); or the like.

In various embodiments, the material comprising the reservoir body 510 may include any of the materials that may make up the outer body 520. Similarly, in various embodiments, the material comprising the outer body 520 may include any of the materials that may make up the reservoir body 510.

Figure 8B:
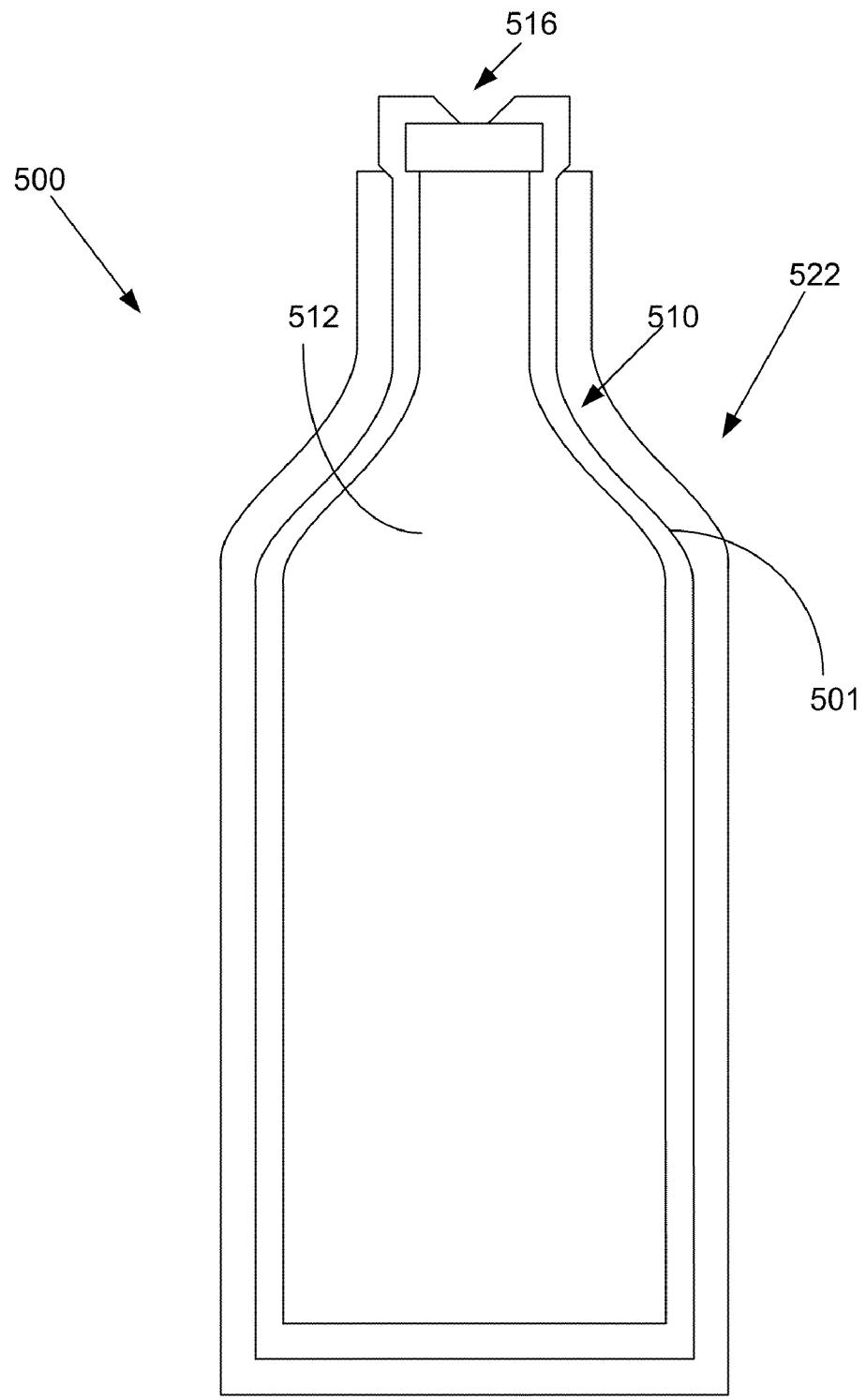
FIG. 8B illustrates a system for containing fluidic media in accordance with an embodiment of the present invention.

Furthermore, in some embodiments, an example of which is illustrated in FIG. 8B, an outer body 522, which may be configured and/or arranged like the outer body 520 (e.g., FIG. 8A), may be required to interact with one or more portions of the reservoir body 510. Thus, in some embodiments, the outer body 522 may be used with only a portion of the reservoir body 510, such as one or more portions where the outer body 522 is required. For example, the outer body 522 may be arranged relative to the reservoir body 510 around areas that may encounter fluidic media contained within the interior volume 512 of the reservoir body 510. In these embodiments, the remainder of the reservoir body 510 may be uncovered by the outer body 522. In yet further embodiments, the outer body 522 may be used with only a portion of the reservoir body 510 where the described advantages are needed.

Figure 8C:
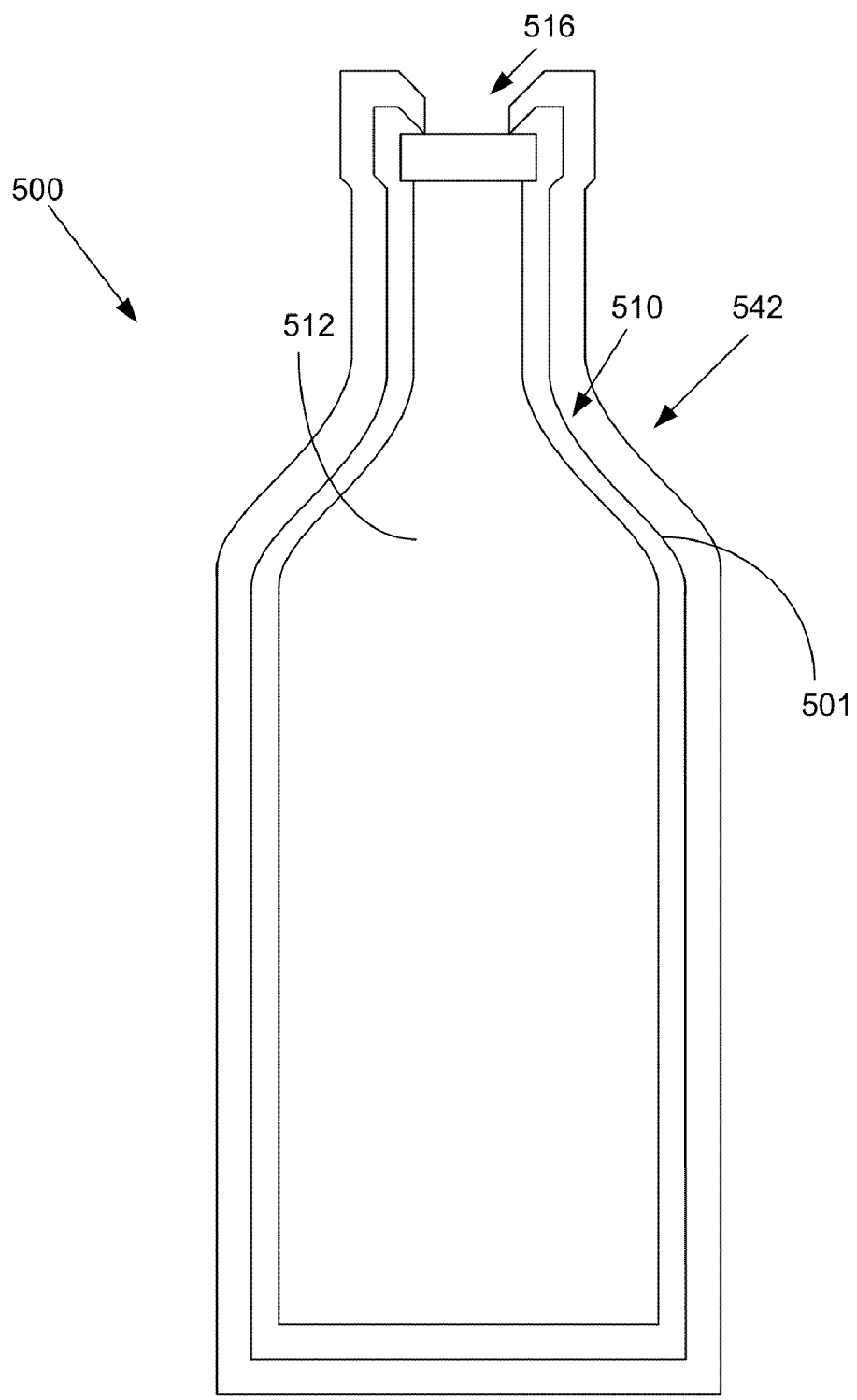
FIG. 8C illustrates a system for containing fluidic media in accordance with an embodiment of the present invention.

In other embodiments, an example of which is illustrated in FIG. 8C, an outer body 542 may be required to interact with a portion of the reservoir body 510 comprising the material of the container wall 501. Thus, for example, the outer body 542 may be used to cover completely the container wall 501 while allowing the remainder of the reservoir body 510, such as a portion of the head portion 516 of the reservoir body 510, to be uncovered.

Figure 8D:
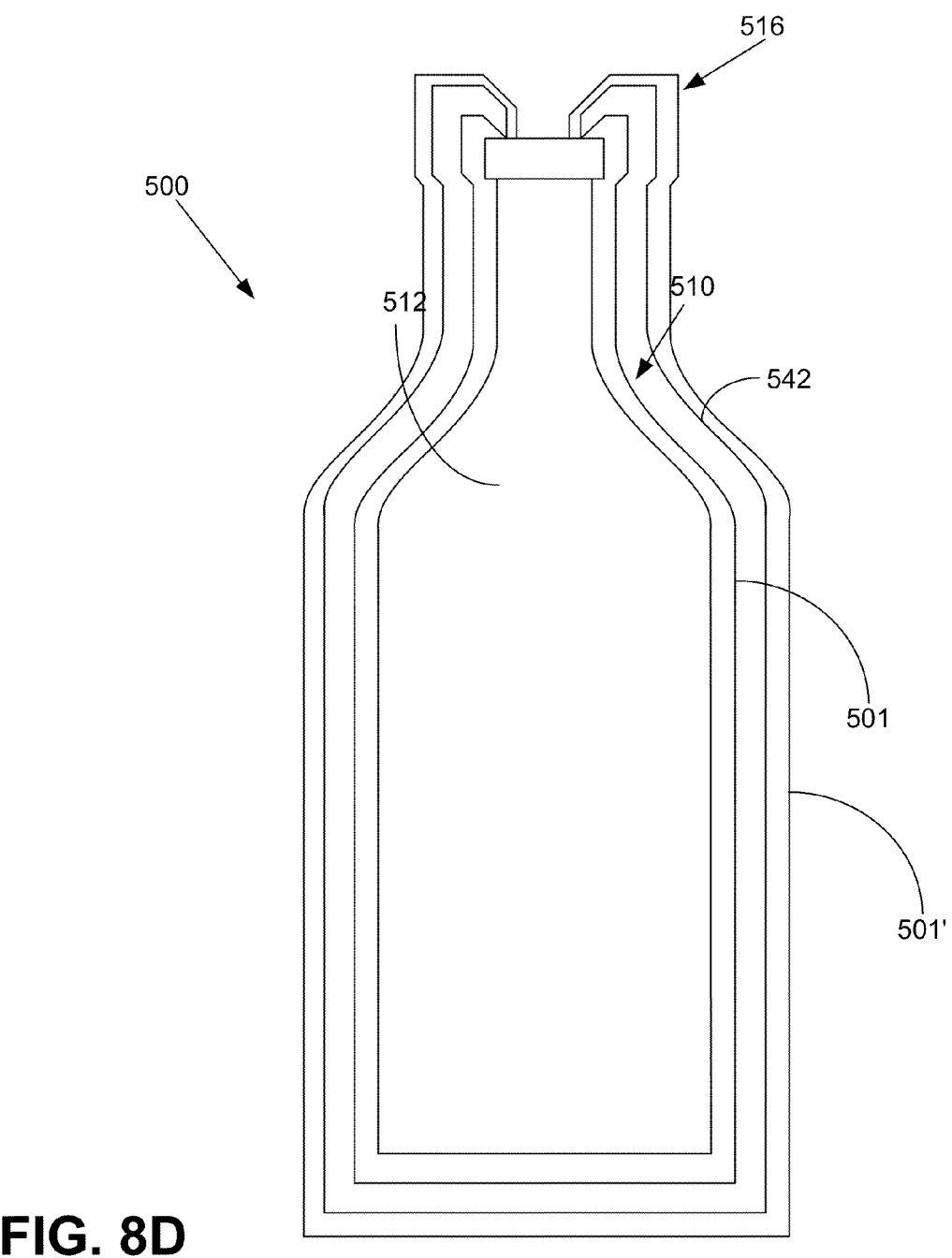
FIG. 8D illustrates a system for containing fluidic media in accordance with an embodiment of the present invention.

Further, in some embodiments, an example of which is illustrated in FIG. 8D, the outer body 542 (520 or 522 in FIGS. 8A-8B) or layer may be sandwiched between a first container wall 501 made of the first material and a second container wall 501' made of the first material (or similar material). Thus, the outer body 542 provided between the first container wall 501 and the second container wall 501' may continue to provide a barrier against diffusion of substances into or out of the reservoir body 510.

Figure 8E:
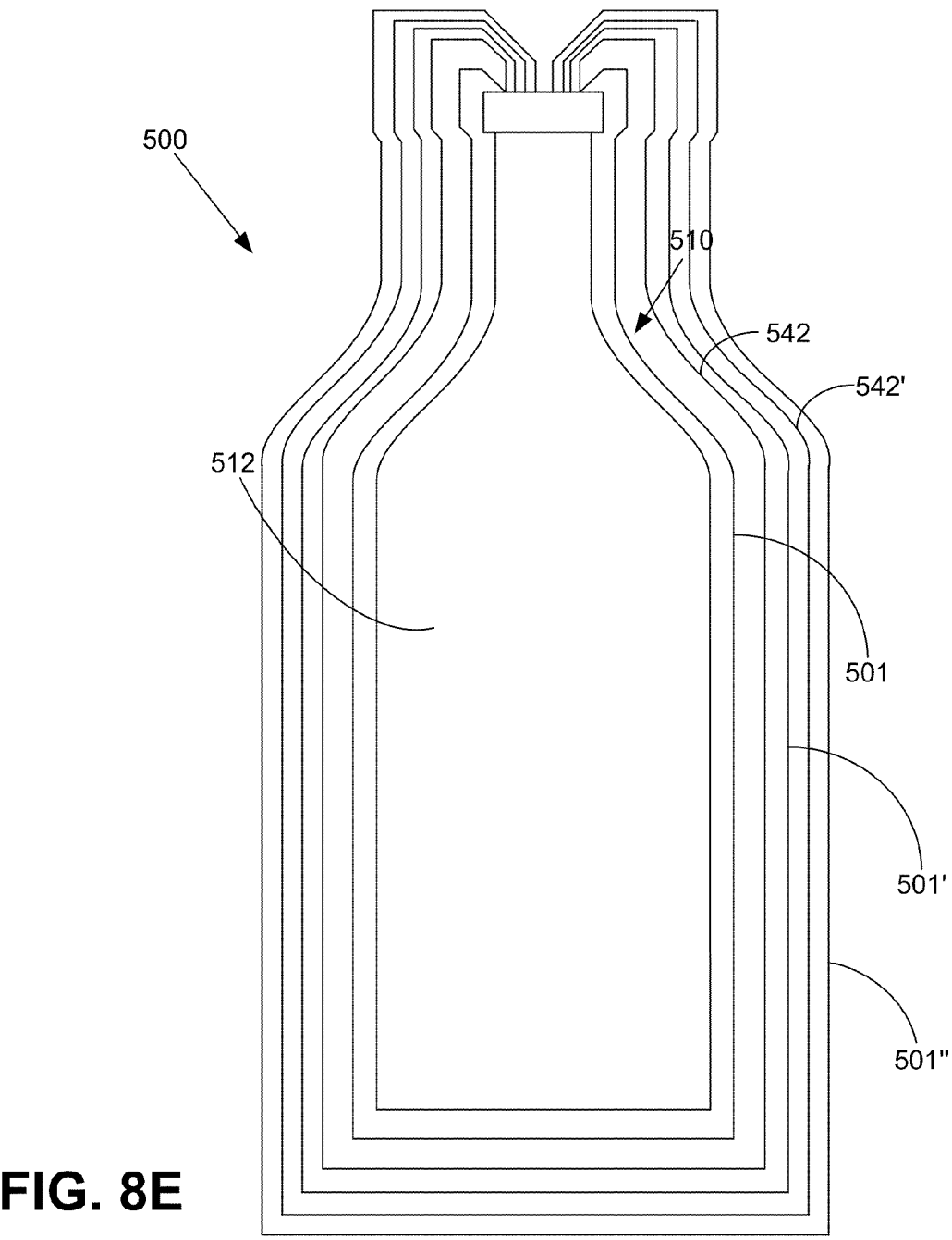
FIG. 8E illustrates a system for containing fluidic media in accordance with an embodiment of the present invention.
Figure 9A:
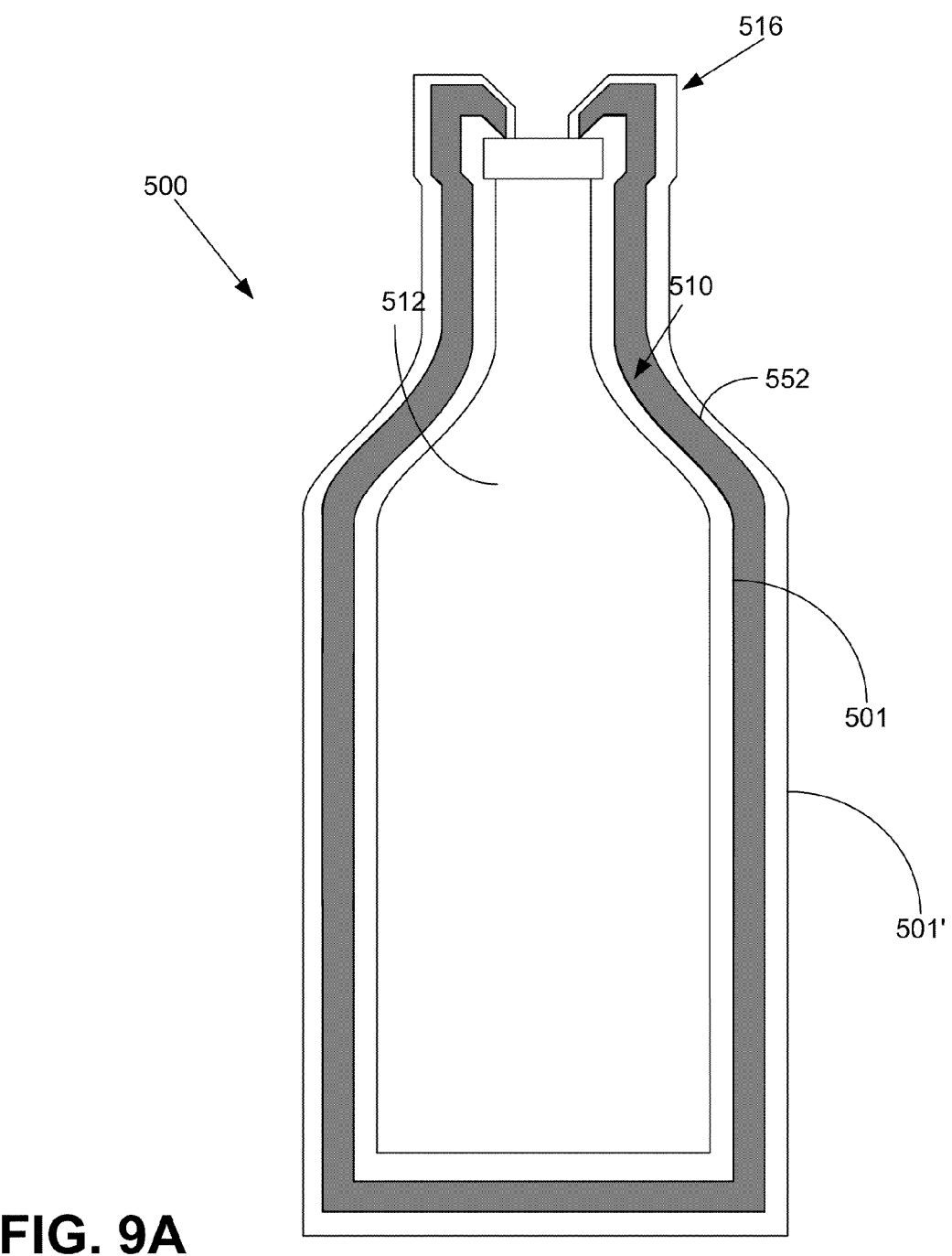
FIG. 9A illustrates a system for containing fluidic media in accordance with an embodiment of the present invention.

In some embodiments, such as the embodiment exemplified in FIG. 9A, the container wall 501 (i.e., the innermost layer) may be made of a cyclic olefin copolymer (or polymer), such as (but not limited to) TOPAS®, or the like. In particular embodiments, the container wall 501 may have a wall thickness of less than 0.3 mm. One or more other layers, such as, but not limited to, the outer body 552 (or layer) (520, 522, 542 in FIGS. 8A-8E) and/or the second container wall 501', may provide structural support or strength to the reservoir system.

In various embodiments, the one or more other layers may or may not be adhered to the container wall 501 or each other. In some embodiments, a space or gap may be provided in between some or all of the one or more other layers and the container wall 501, for example, in which a vacuum or pressurized fluid may be provided. In some embodiments, some or all of the one or more other layers and the container wall 501 may be in contact and, in addition, may or may not be bonded. In some embodiments, some or all of the one or more other layers and the container wall 501 may be extruded together.

In further embodiments, such as the embodiment illustrated in FIG. 8E, multiple outer bodies 542 (made of the same or similar material as each other) and one or more container walls 501 or 501' (made of the same or similar material as each other) may alternate. For example, the outer body 542 (520 or 522 in FIGS. 8A-8B) or layer may be arranged between a first container wall 501 made of the first material and a second container wall 501' made of the first material (or similar material). A second outer body 542' may be arranged between the second container wall 501' and a third container wall 501" made of the first material (or similar material as the first container wall 501 and/or the second container wall 501'). In some embodiments, an outer body (e.g., 542 or 542') may be the outermost layer of the reservoir system.

Figure 9B:
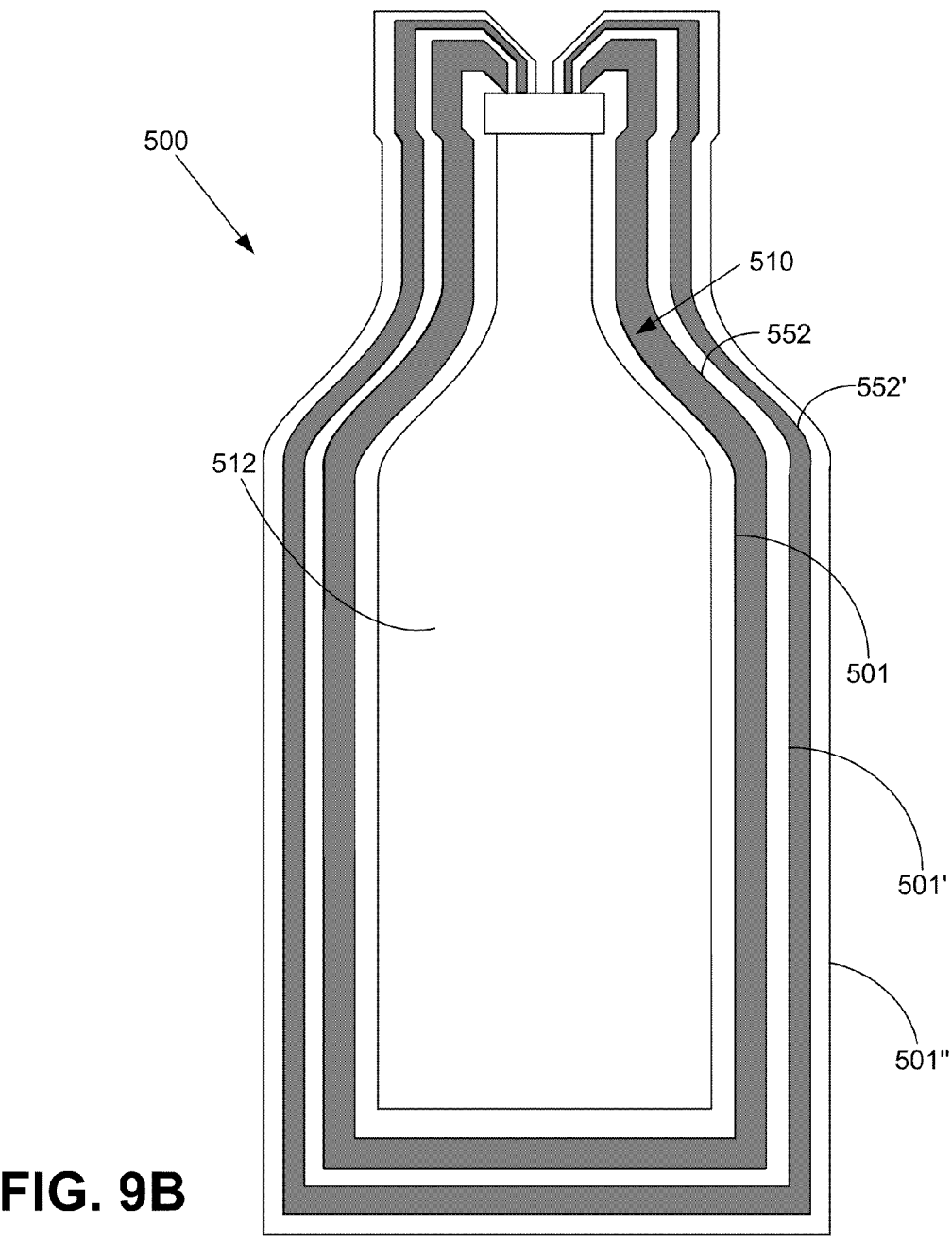
FIG. 9B illustrates a system for containing fluidic media in accordance with an embodiment of the present invention.

In some embodiments, such as the embodiment illustrated in FIG. 9B, the first container wall 501 (i.e., the innermost layer) and the second container wall 501' may be made of a cyclic olefin copolymer (or polymer), such as (but not limited to) TOPAS®, or the like. In particular embodiments, each of the first container wall 501 and the second container wall 501' may have a wall thickness of less than 0.3 mm. One or more other layers, such as, but not limited to, the first outer body 552 (or layer) (520, 522, 542 in FIGS. 8A-8E), the second outer body 552, and/or the third container wall 501" may provide structural support or strength to the reservoir system.

In various embodiments, the one or more other layers may or may not be adhered to one or more of the first container wall 501 and the second container wall 501'. In some embodiments, a space or gap may be provided in between some or all of the one or more other layers and one or more of the first container wall 501 and the second container wall 501', for example, in which a vacuum or pressurized fluid may be provided. In some embodiments, some or all of the one or more other layers and one or more of the first container wall 501 and the second container wall 501' may be in contact and, in addition, may or may not be bonded. In some embodiments, some or all of the one or more other layers and the one or more of the first container wall 501 and the second container wall 501' may be extruded together.

With reference to FIGS. 8A-8E, in some embodiments, the outer body 520 may be a non-permanent layer, such as a casing, packaging material, protective material, or the like adapted to be removed before use of the reservoir body 510 and contents therein. The packaging material may be for inhibiting diffusion/leaching of substances out from the reservoir body 510 during storage of the reservoir body 510. For example, the outer body 520 may be a wrapper to be removed from the reservoir body 510 and then disposed prior to the reservoir body 510 being attached or otherwise used with the delivery device (not shown). Because the fluidic media in the reservoir body 510 presumably will be used relatively soon after the packaging material is removed, there may be less of a need to further inhibit diffusion of substances (e.g., preservatives) out from the reservoir body 510. In further embodiments, the packaging material may be tightly wrapped around or otherwise in firm contact with the reservoir body 510 such that the reservoir body 510 is sufficiently covered to prevent diffusion of substances out from the reservoir body 510.

In some embodiments, an interior layer (not shown) may be provided on an inner surface of the outer body 542 (520 or 522 in FIGS. 8A-8B). For example, the interior layer may be provided between the outer body and the container wall of the reservoir body. The material provided for the interior layer may be hydrophobic or hydrophilic in nature in order to regulate the interaction of infusion formulation components with the inner surface. In some embodiments, an interior or exterior surface of the reservoir body may also contain or be treated to contain chemical groups that permit the covalent or physical attachment of compounds that will regulate its surface properties and permeability.

In other embodiments, the outer body 520 may be a fluid (i.e., gas or liquid) adapted to exert a pressure (e.g., positive pressure) on the reservoir body 510. In such embodiments, the pressure may inhibit diffusion of substances out from the reservoir body 510 and/or inhibit diffusion of substances into the reservoir body 510. In further embodiments, the fluidic media contained in the interior volume 512 of the reservoir body 510 may include preservatives (e.g., cresol, phenol), which may prevent diffusion into the reservoir body 510.

Reservoir systems in accordance with various embodiments of the invention may be manufactured in any suitable manner, including, but not limited to, extruding or molding the container wall and the outer body together or separately. For example, in some embodiments, a surface of the reservoir body may be plasma treated as known in the art. In further embodiments, a lubricant may be applied to the plasma treated surface of the reservoir body. The lubricant may be a silicone-free lubricant, such as, but not limited to, TriboGlide® (manufactured by Tribofilm), or the like. In yet further embodiments, the lubricated surface may be plasma treated. In addition, the container wall and the outer body may be combined in any suitable manner, including, but not limited to, packaging the container wall and the outer body or otherwise manually applying the container wall and outer body together. Various methods of manufacturing a reservoir body and/or components therein (e.g., a plunger head) e are disclosed in, but not limited to, U.S. patent application No. (not yet assigned), entitled "Reservoir Plunger Head Systems and Methods," filed Jul. 31, 2009, herein incorporated by reference in its entirety.

Figure 10A:
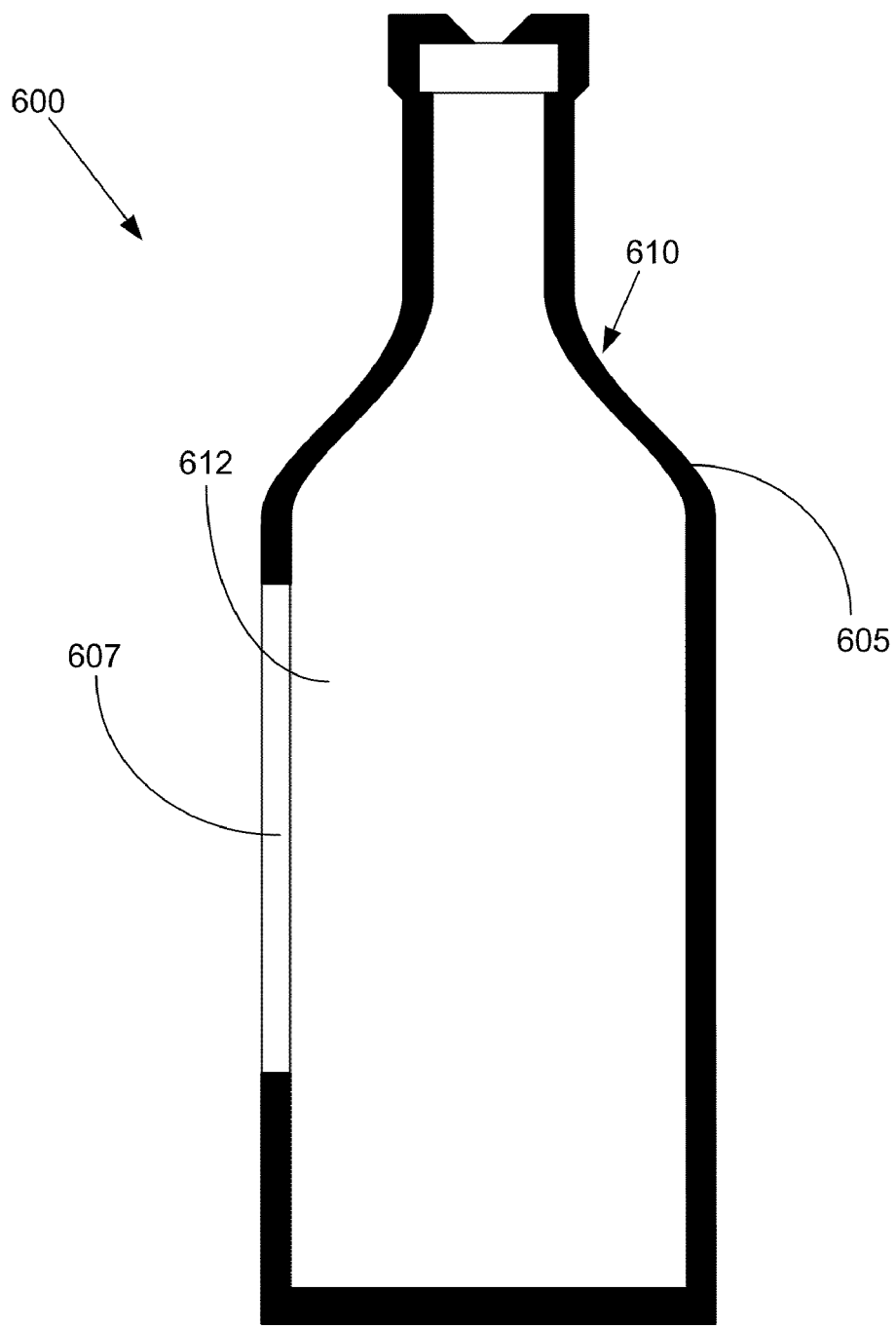
FIG. 10A illustrates a system for containing fluidic media in accordance with an embodiment of the present invention.

FIG. 10A illustrates a reservoir system 600 that may be employed as an embodiment of the reservoir system 40 discussed above, for containing fluidic media in accordance with an embodiment of the present invention. The reservoir system 600 may include, but is not limited to, a reservoir body 610.

The reservoir body 610 may be similar to the reservoir body 510 (e.g., FIGS. 8A-8E). For example, the reservoir body 610 may comprise a container structure having a container wall 605 made of a material similar to the outer body 520, 522, 542, 542' (e.g., FIGS. 8A-8E) or the container wall 501, 501' (e.g., 9A and 9B). The container wall 605 may be shaped or otherwise configured to form the reservoir body 610. The reservoir body 610 may have an interior volume 612 for containing fluidic media, such as, but not limited to, insulin, or the like. The reservoir body 610 may have a port for expelling fluidic media contained in the interior volume 612 of the reservoir body 610.

The reservoir body 610 may be pre-filled with fluidic media prior to the reservoir body 610 being used by a user-patient. The reservoir body 610 may be adapted to store fluidic media for a specific duration of time, for example days, weeks, months, or longer depending on needs of user-patients. The reservoir body 610 may be of any suitable shape and/or size and may be adapted to hold any volume depending on needs of user-patients. In various embodiments, the reservoir body 610 may be adapted to store fluidic media external to the human body.

The container wall 605 may be for inhibiting diffusion of substances into and/or out of the interior volume 612 of the reservoir body 610. Thus, the properties, composition, and/or stability of fluidic media contained within the interior volume 612 of the reservoir body 610 may be more accurately maintained, controlled, and/or monitored. In some embodiments, the container wall 605 may be for inhibiting an outward diffusion of preservatives within fluidic media contained in the interior volume 612 of the reservoir body 610. In further embodiments, the container wall may be for regulating an interaction between fluidic media contained in the interior volume 612 of the reservoir body 610 and the outer body 620, for example through the use of hydrophobic or hydrophilic materials. In some embodiments, the container wall 605 may be made of (or treated with) a cyclic olefin copolymer (or polymer), such as TOPAS®, or the like.

In some embodiments, the container wall 605 may be formed or otherwise adapted to be opaque to limit partially or completely an amount of light from passing through the container wall 605 (e.g., through opposing wall sections of the container wall 605 and the interior volume 612). For example, the container wall 605 may have a light transmission at 400 nm of less than 25% through the reservoir body (e.g., through both of the container walls 605 of the reservoir body 610 and the interior volume 612 of the reservoir body 610) relative to air in a case where the interior volume 612 contains water.

In further embodiments, the container wall 605 may be provided with a window 607 for allowing contents in the interior volume 612 of the reservoir body 610 to be viewable. In such embodiments, the entire container wall 605 may be opaque except for the viewing window 607. Allowing light to enter into the interior volume 612 of the reservoir body 610, for example, may allow a user-patient to view contents (e.g., fluidic media) in the interior volume 612 of the reservoir body 610 to determine an amount contained in the interior volume 612 and/or look for a presence of bubbles, contaminants, crystallized particles, or the like.

In various embodiments, multiple windows 607 may be provided along the container wall 605. For example, each window may be provided at a location of or corresponding to a fill gradient or other visual indicator. Thus, a user-patient can determine approximately how much fluidic media is contained within the interior volume 612 of the reservoir body 610.

Figure 10B:
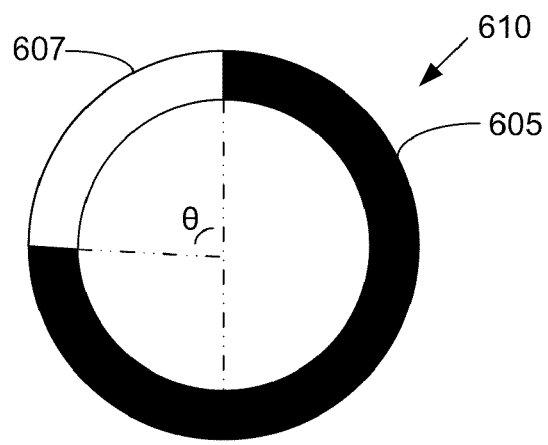
FIG. 10B illustrates a cross-section of a system for containing fluidic media in accordance with an embodiment of the present invention.

In some embodiments, the window(s) 607 may be sized, configured, and/or arranged to provide a viewing angle $\theta$ of less than a 90° relative to a central axis of the reservoir body 610 as shown for example in FIG. 10B. In some embodiments, the window 607 may have a width dimension extending partially around a central axis of the reservoir body 610. The width dimension may be between a first width edge and a second width edge. The first width edge may be linearly spaced from the central axis of the reservoir body 610 in a first linear dimension, and the second width edge may be linearly spaced from the central axis of the reservoir body 610 in a second linear dimension. The first linear dimension and the second linear dimension may be at an angle of less than 90° relative to each other. Thus, in various embodiments, a user-patient looking into a window 607 may be limited to looking into the interior volume 612 of the reservoir body 610. Accordingly, the user-patient may not be able to see completely through the reservoir body 610.

Figure 10C:
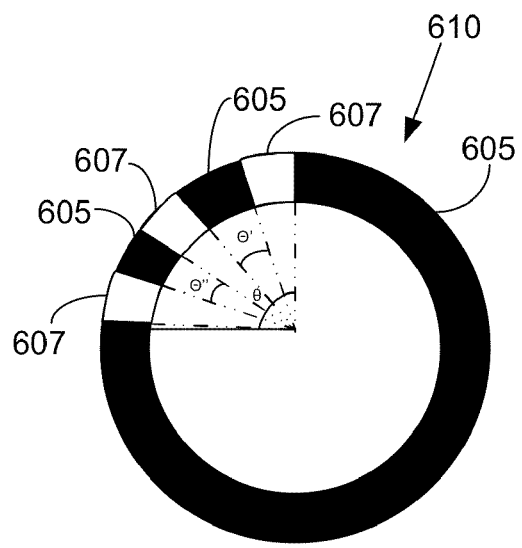
FIG. 10C illustrates a cross-section of a system for containing fluidic media in accordance with an embodiment of the present invention.
Figure 10D:
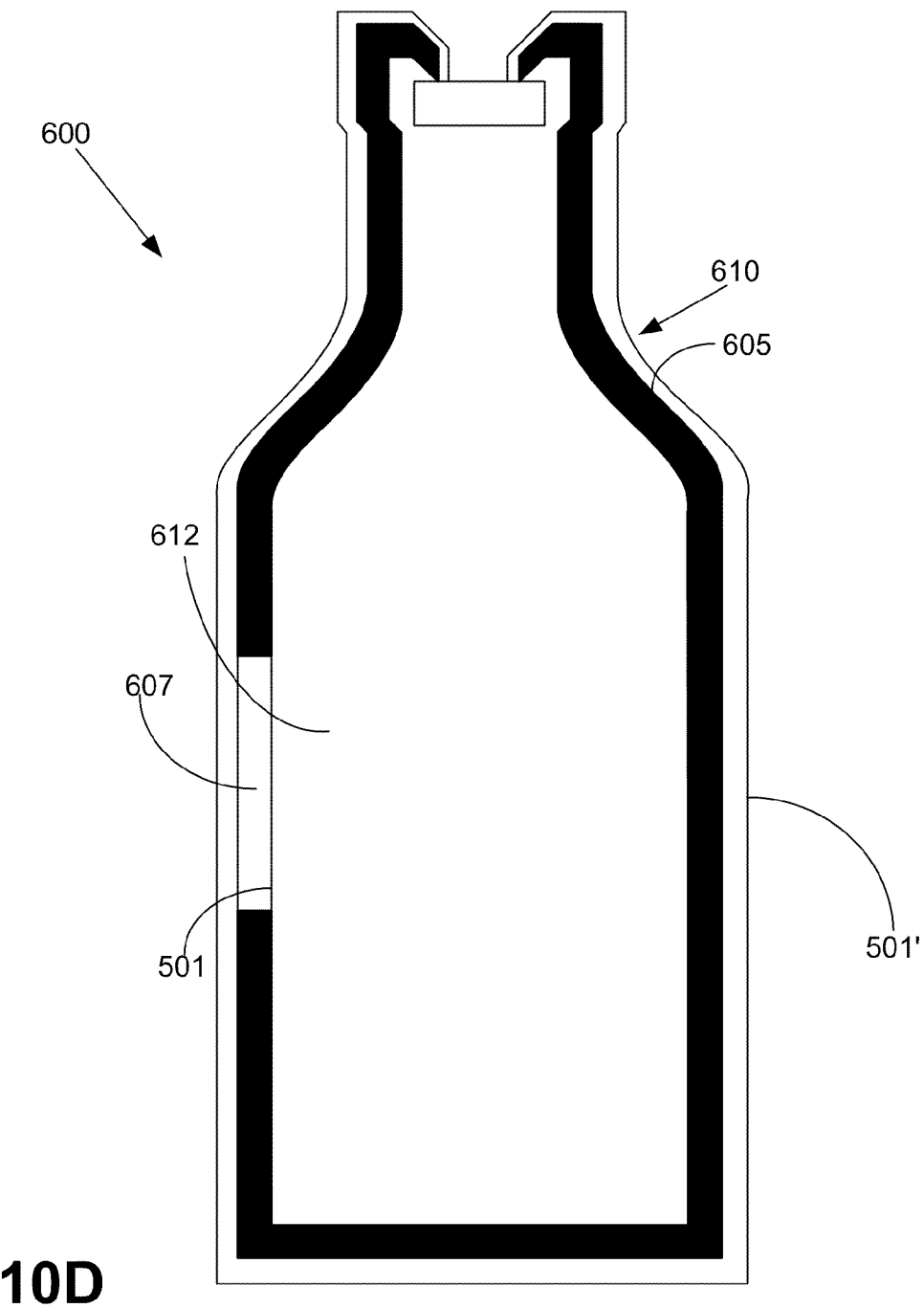
FIG. 10D illustrates a system for containing fluidic media in accordance with an embodiment of the present invention.

In some embodiments, such as the embodiment exemplified in FIG. 10C, multiple windows 607 may be sized, configured, and/or arranged around the reservoir body 610 less than 90° apart from each other (relative to an axis of the reservoir body 610). For example, one pair of windows may be separated by an angle $\theta'$ and another pair may be separated by an angle $\theta''$, which may or may not have the same magnitude as angle $\theta'$. In further embodiments, the multiples windows 607 may be sized, configured, and/or arranged so that collectively the windows 607 provide a viewing angle $\theta$ of less than a 90°.

With reference to FIGS. 9A-10C, in embodiments with multiple layers (e.g., FIGS. 9A and 9B), at least one of the layers may be arranged or otherwise adapted similar to container wall 605 (e.g., FIGS. 10A-10C). That is, as exemplified in FIG. 10D, a reservoir body 610 having multiple layers may include at least one opaque layer (e.g., 605) provided with a viewing window 607 as previously described.

With reference to FIGS. 9A-10D, in various embodiments, the reservoir body 510 (or 610) may be textured, etched, or otherwise frosted to reduce visibility through the material of the container wall (e.g., 605). Such a frosted reservoir body (not shown) may be formed during a molding process and/or through a chemical reaction. In some embodiments, the frosted reservoir body may be provided with a window, such as the window 607, to allow contents within the frosted reservoir to be visible to a user-patient or the like, as previously described.

In various embodiments, the reservoir body may be configured to be opaque and/or frosted in a manner previously described to a point where light cannot pass through the reservoir body (i.e., passing through the walls of the reservoir body), for example, as previously described. The reservoir body may include a plunger head or portions/components (e.g., seal members) thereof within the reservoir body adapted to be visible through a wall of the reservoir body. For example, the reservoir body may be frosted white (or any other suitable shade or color), which may allow a black seal member of the plunger head to be visible through the wall of the reservoir body. Accordingly, a user-patient may be able to determine approximately an amount of fluidic media within the reservoir body by determining a position of the black seal member. As a further example, each seal member of the plunger head may have a different color and/or visibility through the wall of a white (or any other suitable shade or color) frosted reservoir body. Accordingly, one or more of the seal members may be distinguishable from the other(s).

In various embodiments, the reservoir body may be configured, adapted, or otherwise formed of a material reactable with contents in the interior volume of the reservoir body. For example, the reservoir body may be adapted to change in color, temperature, condensation level, or otherwise provide an indicator for indicating fluid level or an amount of fluidic media within the interior volume of the reservoir body along locations in contact with the contents within the interior volume of the reservoir body. In various embodiments, the reservoir body may include a detecting mechanism for determining a level or amount of fluidic media in the interior volume of the reservoir body and/or a position of the plunger head or portion(s) thereof. For example, the plunger head may be provided with a magnet arranged to be detectable by the detecting mechanism to determine a position of the plunger head that may correspond to the amount of fluidic media within the interior volume of the reservoir body.

In various embodiments, it should be noted that reservoir systems employing a multiple layer configuration as described throughout may include any suitable configuration having one or more layers, which, for example, may be layers or sheets that may or may not be in contact, firm contact, bonded, adjacent, adherable to each other, removable, or the like. Similarly, a multiple layer configuration may include any suitable configuration including a main body (e.g., reservoir body 510) as a first (or other) layer and an enclosure (e.g., packaging material or a casing, such as 102 in FIG. 7) as a second (or other) layer. In other words, references in the disclosure to a wall, layer, or body are not limited to their respective definitions, but in addition may or may not be synonymous with each other.

Figure 11:
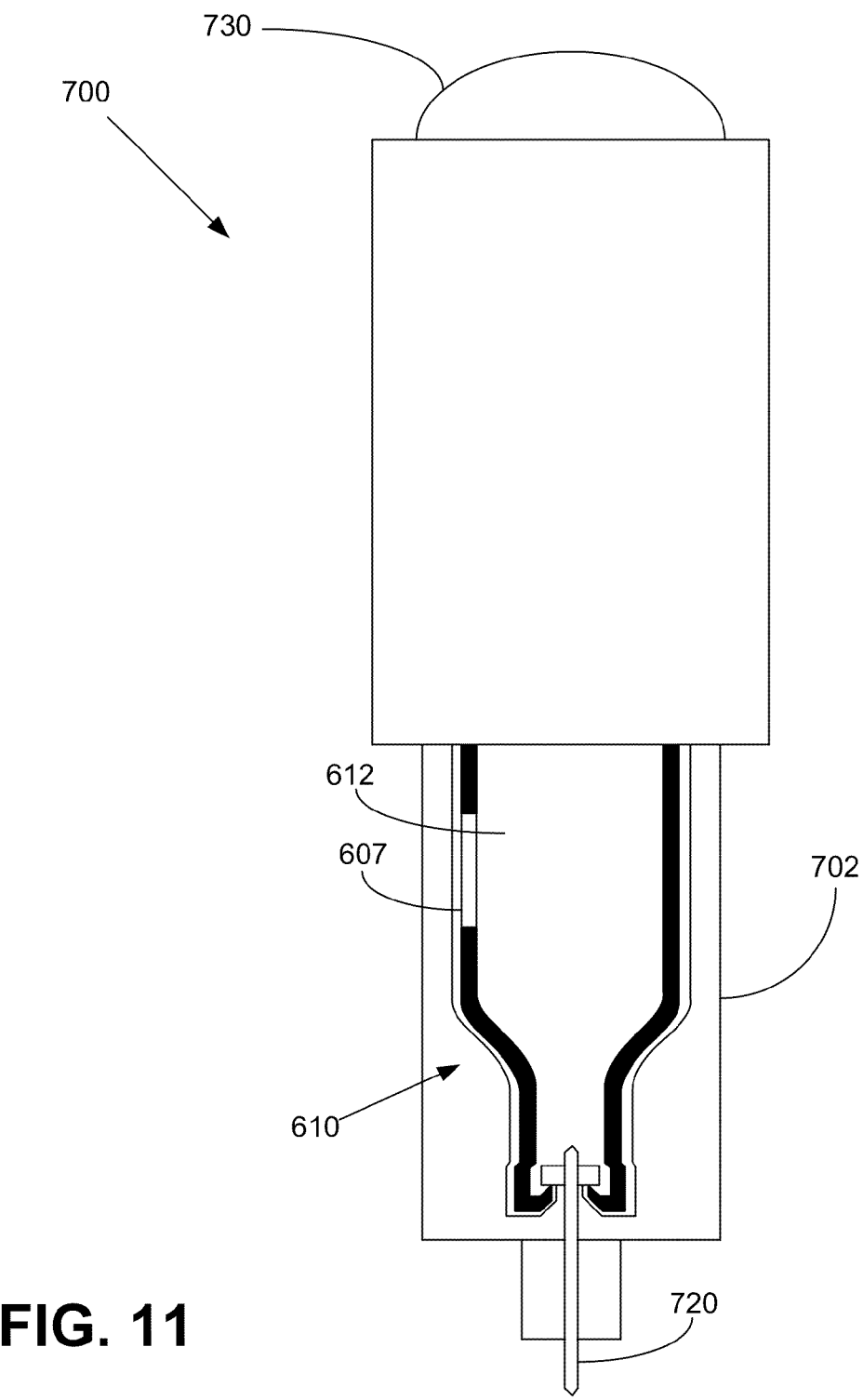
FIG. 11 illustrates a system for delivering fluidic media in accordance with an embodiment of the present invention.

FIG. 11 illustrates a delivery device 700 according to an embodiment of the present invention. The delivery device 700 may be an insulin pen or similar pen-like injection device or any other pump device used in a hospital or medical environment. According to some embodiments, the delivery device 700 may include, but is not limited to, a housing 702, the reservoir body 510 or 610 (e.g., FIGS. 8A-10D), and a drive mechanism (not shown). Other examples of pen-like injection devices and other similar devices are disclosed in, but are not limited to, U.S. Pat. Nos. 5,599,323; 5,626,566; 5,683,361; 6,302,855; 6,454,746; 7,104,972; U.S. Patent App. Pub. No. US 2007/0244445; U.S. Patent App. Pub. No. US 2008/0065026; U.S. Patent App. Pub. No. US 2008/0097322, all of which are herein incorporated by reference. The housing 702 may be made of any suitably rigid material, such as (but not limited) plastic, glass, ceramic, metal, composite material, and/or the like.

With reference to FIGS. 8A-11, the housing 702 may contain the reservoir body 610 (or 510) or any other reservoir as previously described. Thus, for example, the reservoir body 610 may comprise a container structure having a container wall (e.g., 605) shaped to form the reservoir body 610. The container wall may be made of (or treated with) a material comprising a cyclic olefin copolymer (or polymer) material, such as (but not limited to) TOPAS®, or the like. The container wall or a portion thereof may be for formed or otherwise adapted to be opaque to limit partially or completely an amount of light passing through the reservoir body 610. As previously described, in some embodiments, the container wall 605 may be provided with a window 607 for allowing contents in the interior volume 612 of the reservoir body 610 to be viewable. In such embodiments, the entire container wall 605 may be opaque except for the viewing window 607. In further embodiments, the housing 702 may be provided with a window (not shown) at least partially aligned with the window 607 of the reservoir body 610 for allowing contents in the interior volume 612 of the reservoir body 610 to be viewable. For example, the window of the housing 702 may be facing and adjacent the window 607 of the reservoir body 610. In other embodiments, the housing 702 may be sufficiently clear or otherwise transparent to allow the window 607 of the reservoir body 610 to be viewable, and thus allow the contents in the interior volume 612 of the reservoir body 610 to be viewable.

The reservoir body 610 may have an outlet 720 for expelling fluidic media contained in the interior volume 612 of the reservoir body 610. The outlet 720 may be a needle, tubing, or other fluid conduit for allowing fluidic media contained in the interior volume 612 of the reservoir body 610 to be expelled to a user-patient. In some embodiments, the reservoir body 610 may be a cartridge or other container configured to be removable from the housing 602, for example, when the reservoir body has been sufficiently (but not necessarily) depleted, and replaceable with a new reservoir body.

The drive mechanism (not shown) may be adapted to force fluidic media from the interior volume 612 of the reservoir body 610 and out the outlet 720 upon activation of the drive mechanism, for example, by operating a trigger 730, button, or the like. For instance, a plunger (not shown) operatively connected with a bias member (not shown) and a trigger 730 or the like may be provided in the housing to selectively force fluidic media contained in the interior volume 612 from the interior volume 612 of the reservoir body 610 and out the outlet 720. Various examples of drive mechanisms are disclosed in European Patent Publication No. 730876A2; U.S. Pat. Nos. 5,599,323; 5,626,566; 5,683,361; 6,302,855; 6,454,746; 7,104,972; U.S. Patent App. Pub. No. US 2007/0244445; U.S. Patent App. Pub. No. US 2008/0065026; U.S.

Patent App. Pub. No. US 2008/0097322, all of which are herein incorporated by reference.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system for delivering fluidic media, the system comprising:
    a housing;
    a reservoir disposed within the housing, the reservoir having at least one wall bordering an interior volume for containing fluidic media, the wall being made of a material comprising a cyclic olefin copolymer, the material of the wall is treated with a treatment that substantially prevents light from passing through the material of the wall;
    a plunger head arranged for movement in the interior volume of the reservoir to expel fluidic media from the interior volume of the reservoir; and
    a fluid conduit in communication with the interior volume of the reservoir for allowing fluidic media contained in the interior volume to be expelled from the reservoir with movement of the plunger head.

2. The system of claim 1, wherein the fluid conduit comprises a needle.

3. The system of claim 1, wherein the reservoir is removable from the housing.

4. The system of claim 1, the wall comprising at least one layer made of a material that is not a cyclic olefin copolymer.

5. The system of claim 1, wherein the wall is opaque to substantially prevent light from passing through the material of the wall.

6. The system of claim 1, wherein the treatment of the material of the wall is at least one of being frosted, textured, and etched to substantially prevent light from passing through the material of the wall.

7. The system of claim 1, the wall having a light transmission at 400 nm of less than 25%.

8. The system of claim 1, the wall of the reservoir having at least one window for allowing light to pass into the interior volume of the reservoir.

9. The system of claim 8, the reservoir having a circular cross-section circumference, the at least one window having a width dimension corresponding to less than a quarter of the circular cross-section circumference.

10. The system of claim 8, the at least one window having a width dimension corresponding to an angle of less than 90° relative to a central axis of the reservoir.

11. The system of claim 8, the at least one window for providing a viewing angle into the interior volume of the reservoir of less than 90° relative to a central axis of the reservoir.

12. The system of claim 8, wherein the at least one window comprises a plurality of windows, each of the plurality of windows offset less than 90° relative to a central axis of the reservoir from any other window of the plurality of windows.

13. The system of claim 8, wherein the housing is sufficiently transparent for allowing light to pass through the housing and the window in the reservoir into the interior volume of the reservoir.

14. The system of claim 8, the housing having at least one window for allowing light to pass through the at least one window of the housing and the at least one window in the reservoir into the interior volume of the reservoir.

15. The system of claim 14, wherein the at least one window of the housing is adjacent and facing the at least one window of the reservoir.

16. The system of claim 8,
    the window having a width dimension extending partially around a central axis of the reservoir, the width dimension between a first width edge and a second width edge;
    wherein the first width edge is linearly spaced from the central axis of the reservoir in a first linear dimension, and the second width edge is linearly spaced from the central axis of the reservoir in a second linear dimension; and
    wherein the first linear dimension and the second linear dimension are at an angle of less than 90° relative to each other.

17. The system of claim 1, the system further comprising:
    a drive mechanism for forcing fluidic media from the interior volume out the fluid conduit in a case where the interior volume contains fluidic media and the drive mechanism is activated.

18. A method of manufacturing a system for delivering fluidic media, the system comprising:
    providing a housing;
    providing a reservoir having at least one wall bordering an interior volume for containing fluidic media, the wall being made of a material comprising a cyclic olefin copolymer;
    treating the material of the wall of the reservoir with a treatment to substantially prevent light from passing through the material of the wall;
    disposing the reservoir within the housing;
    arranging a plunger head for movement in the interior volume of the reservoir to expel fluidic media from the interior volume of the reservoir; and
    providing a fluid conduit in communication with the interior volume for allowing fluidic media contained in the interior volume of the reservoir to be expelled from the reservoir with movement of the plunger head.

19. The method of claim 18, the wall of the reservoir having at least one window for allowing light to pass into the interior volume of the reservoir.

20. The system of claim 1, wherein the plunger head is in contact with the wall made of the cyclic olefin copolymer material.

21. The system of claim 2, wherein the needle is for insertion into a human to deliver fluidic media from the interior volume of the reservoir when the fluidic media is expelled from the reservoir with movement of the plunger head.

22. The system of claim 1, wherein the fluidic media is an infusion medium.

23. The method of claim 18, wherein the treatment being at least one of being frosted, textured, and etched to substantially prevent light from passing through the material of the wall.

24. The system of claim 1, wherein the material of the wall is treated with a surface treatment that causes the material of the wall to prevent passage of light.

25. The system of claim 1, wherein the material of the wall that is treated has a surface that is uncovered.

26. The system of claim 1, wherein the material of the wall has a surface and the treatment comprises a surface treatment that prevents light from passing through the wall.

* * * * *